(12) United States Patent
Yamada et al.

(10) Patent No.: US 9,366,261 B2
(45) Date of Patent: Jun. 14, 2016

(54) CENTRIFUGAL PUMP DEVICE

(71) Applicant: Thoratec Corporation, Pleasanton, CA (US)

(72) Inventors: Hiroyuki Yamada, Shizuoka (JP); Ken Sugiura, Shizuoka (JP)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 14/372,998

(22) PCT Filed: Jan. 9, 2013

(86) PCT No.: PCT/JP2013/050187
§ 371 (c)(1),
(2) Date: Aug. 28, 2014

(87) PCT Pub. No.: WO2013/108681
PCT Pub. Date: Jul. 25, 2013

(65) Prior Publication Data
US 2015/0010415 A1    Jan. 8, 2015

(30) Foreign Application Priority Data

Jan. 18, 2012 (JP) ................. 2012-007845

(51) Int. Cl.
*F04D 29/04* (2006.01)
*F04D 25/02* (2006.01)
(Continued)

(52) U.S. Cl.
CPC ............. *F04D 25/026* (2013.01); *A61M 1/101* (2013.01); *A61M 1/1015* (2014.02);
(Continued)

(58) Field of Classification Search
CPC . A61M 1/101; A61M 1/1015; A61M 1/1017; A61M 1/1031; F16C 32/0402; F16C 33/107; F04D 13/0666; F04D 29/048; F04D 29/0413; H02K 5/1282; H02K 21/24; H02K 7/14
USPC ................. 417/352, 353, 365, 423.7, 423.14, 417/424.1, 424.2; 310/87, 216.045; 600/16
See application file for complete search history.

(56) References Cited

U.S. PATENT DOCUMENTS 1,093,868 A     4/1914    Leighty
2,684,035 A     7/1954    Kemp
(Continued)

FOREIGN PATENT DOCUMENTS

CN     102239334 A     11/2011
CN     102341600 A     2/2012
(Continued)

OTHER PUBLICATIONS

Asama, at al., "Suspension Performance of a Two-Axis Actively Regulated Consequent-Pole Bearingless Motor," IEEE Transactions On Energy Conversion, vol. 28, No. 4, Dec. 2013, 8 pages.
(Continued)

*Primary Examiner* — Patrick Hamo
(74) *Attorney, Agent, or Firm* — Kilpatrick Townsend & Stockton LLP

(57) ABSTRACT

This centrifugal blood pump device comprises an impeller which is provided within a blood chamber, a permanent magnet which is provided to one surface of the impeller, a permanent magnet which is provided to the inner wall of the blood chamber, permanent magnets which are provided to the other surface of the impeller, and multiple sets of magnetic bodies and coils, which are disposed within a motor chamber and which rotationally drive the impeller with a partition wall located between the impeller and the sets of magnetic bodies and coils. The magnetic bodies are formed in a solid cylindrical shape. The configuration enables the impeller to be smoothly activated for rotation by controlling a coil current.

17 Claims, 32 Drawing Sheets

(51) Int. Cl.
*F04D 29/048* (2006.01)
*F04D 13/06* (2006.01)
*A61M 1/10* (2006.01)
*F04D 17/10* (2006.01)
*A61M 1/12* (2006.01)

(52) U.S. Cl.
CPC .......... *A61M 1/1031* (2014.02); *F04D 13/064* (2013.01); *F04D 13/0666* (2013.01); *F04D 17/10* (2013.01); *F04D 29/048* (2013.01); *A61M 1/122* (2014.02)

(56) References Cited

U.S. PATENT DOCUMENTS

| | | | |
|---|---|---|---|
| 3,510,229 | A | 5/1970 | Smith |
| 3,932,069 | A | 1/1976 | Giardini et al. |
| 3,960,468 | A | 6/1976 | Boorse et al. |
| 4,149,535 | A | 4/1979 | Voider |
| 4,382,199 | A | 5/1983 | Isaacson |
| 4,392,836 | A | 7/1983 | Sugawara |
| 4,507,048 | A | 3/1985 | Belenger et al. |
| 4,540,402 | A | 9/1985 | Aigner |
| 4,549,860 | A | 10/1985 | Yakich |
| 4,686,982 | A | 8/1987 | Nash |
| 4,688,998 | A | 8/1987 | Olsen et al. |
| 4,753,221 | A | 6/1988 | Kensey et al. |
| 4,769,006 | A | 9/1988 | Papatonakos |
| 4,790,843 | A | 12/1988 | Carpentier et al. |
| 4,806,080 | A | 2/1989 | Mizobuchi et al. |
| 4,817,586 | A | 4/1989 | Wampler |
| 4,846,152 | A | 7/1989 | Wampler et al. |
| 4,895,557 | A | 1/1990 | Moise et al. |
| 4,900,227 | A | 2/1990 | Troup lin |
| 4,902,272 | A | 2/1990 | Milder et al. |
| 4,906,229 | A | 3/1990 | Wampler |
| 4,908,012 | A | 3/1990 | Moise et al. |
| 4,919,647 | A | 4/1990 | Nash |
| 4,930,997 | A | 6/1990 | Bennett |
| 4,944,722 | A | 7/1990 | Carriker et al. |
| 4,957,504 | A | 9/1990 | Chardack |
| 4,969,865 | A | 11/1990 | Hwang et al. |
| 4,985,014 | A | 1/1991 | Orejola |
| 4,995,857 | A | 2/1991 | Arnold |
| 5,092,844 | A | 3/1992 | Schwartz et al. |
| 5,092,879 | A | 3/1992 | Jarvik |
| 5,106,263 | A | 4/1992 | Irie |
| 5,106,273 | A | 4/1992 | Lemarquand et al. |
| 5,106,372 | A | 4/1992 | Ranford |
| 5,112,202 | A | 5/1992 | Ozaki et al. |
| 5,112,349 | A | 5/1992 | Summers et al. |
| 5,129,883 | A | 7/1992 | Black |
| 5,145,333 | A | 9/1992 | Smith |
| 5,147,186 | A | 9/1992 | Buckholtz |
| 5,190,528 | A | 3/1993 | Fonger et al. |
| 5,201,679 | A | 4/1993 | Velte et al. |
| 5,211,546 | A | 5/1993 | Isaacson et al. |
| 5,275,580 | A | 1/1994 | Yamazaki |
| 5,290,227 | A | 3/1994 | Pasque |
| 5,290,236 | A | 3/1994 | Mathewson |
| 5,306,295 | A | 4/1994 | Kolff et al. |
| 5,312,341 | A | 5/1994 | Turi |
| 5,332,374 | A | 7/1994 | Kricker et al. |
| 5,346,458 | A | 9/1994 | Afield |
| 5,354,331 | A | 10/1994 | Schachar |
| 5,360,445 | A | 11/1994 | Goldowsky |
| 5,370,509 | A | 12/1994 | Golding et al. |
| 5,385,581 | A | 1/1995 | Bramm et al. |
| 5,405,383 | A | 4/1995 | Barr |
| 5,449,342 | A | 9/1995 | Hirose et al. |
| 5,478,222 | A | 12/1995 | Heidelberg et al. |
| 5,504,978 | A | 4/1996 | Meyer, III |
| 5,507,629 | A | 4/1996 | Jarvik |
| 5,533,957 | A | 7/1996 | Aldea |
| 5,569,111 | A | 10/1996 | Cho et al. |
| 5,575,630 | A | 11/1996 | Nakazawa et al. |
| 5,595,762 | A | 1/1997 | Derrieu et al. |
| 5,611,679 | A | 3/1997 | Ghosh et al. |
| 5,613,935 | A | 3/1997 | Jarvik |
| 5,643,226 | A | 7/1997 | Cosgrove et al. |
| 5,678,306 | A | 10/1997 | Bozeman, Jr. et al. |
| 5,692,882 | A | 12/1997 | Bozeman, Jr. et al. |
| 5,695,471 | A | 12/1997 | Wampler |
| 5,725,357 | A | 3/1998 | Nakazeki et al. |
| 5,738,649 | A | 4/1998 | Macoviak |
| 5,746,575 | A | 5/1998 | Westphal et al. |
| 5,746,709 | A | 5/1998 | Rom et al. |
| 5,749,855 | A | 5/1998 | Reitan |
| 5,755,784 | A | 5/1998 | Jarvik |
| 5,776,111 | A | 7/1998 | Tesio |
| 5,800,559 | A | 9/1998 | Higham et al. |
| 5,807,311 | A | 9/1998 | Palestrant |
| 5,814,011 | A | 9/1998 | Corace |
| 5,824,069 | A | 10/1998 | Lemole |
| 5,851,174 | A | 12/1998 | Jarvik et al. |
| 5,853,394 | A | 12/1998 | Tolkoff et al. |
| 5,868,702 | A | 2/1999 | Stevens et al. |
| 5,868,703 | A | 2/1999 | Bertolero et al. |
| 5,890,883 | A | 4/1999 | Golding et al. |
| 5,924,848 | A | 7/1999 | Izraelev |
| 5,924,975 | A | 7/1999 | Goldowsky |
| 5,928,131 | A | 7/1999 | Prem |
| 5,938,412 | A | 8/1999 | Israelev |
| 5,941,813 | A | 8/1999 | Sievers et al. |
| 5,947,703 | A | 9/1999 | Nojiri et al. |
| 5,951,263 | A | 9/1999 | Taylor et al. |
| 5,964,694 | A | 10/1999 | Siess et al. |
| 6,004,269 | A | 12/1999 | Crowley et al. |
| 6,007,479 | A | 12/1999 | Rottenberg et al. |
| 6,030,188 | A | 2/2000 | Nojiri et al. |
| 6,042,347 | A | 3/2000 | Scholl et al. |
| 6,053,705 | A | 4/2000 | Schob et al. |
| 6,058,593 | A | 5/2000 | Siess |
| 6,066,086 | A | 5/2000 | Antaki et al. |
| 6,071,093 | A | 6/2000 | Hart |
| 6,074,180 | A | 6/2000 | Khanwilkar et al. |
| 6,080,133 | A | 6/2000 | Wampler |
| 6,082,900 | A | 7/2000 | Takeuchi et al. |
| 6,086,527 | A | 7/2000 | Talpade |
| 6,100,618 | A | 8/2000 | Schoeb et al. |
| 6,123,659 | A | 9/2000 | leBlanc et al. |
| 6,123,726 | A | 9/2000 | Mori et al. |
| 6,139,487 | A | 10/2000 | Siess |
| 6,142,752 | A | 11/2000 | Akamatsu et al. |
| 6,143,025 | A | 11/2000 | Stobie et al. |
| 6,146,325 | A | 11/2000 | Lewis et al. |
| 6,149,683 | A | 11/2000 | Lancisi et al. |
| 6,158,984 | A | 12/2000 | Cao et al. |
| 6,171,078 | B1 | 1/2001 | Schob |
| 6,176,822 | B1 | 1/2001 | Nix et al. |
| 6,176,848 | B1 | 1/2001 | Rau et al. |
| 6,190,304 | B1 | 2/2001 | Downey et al. |
| 6,206,659 | B1 | 3/2001 | Izraelev |
| 6,227,797 | B1 | 5/2001 | Watterson et al. |
| 6,227,820 | B1 | 5/2001 | Jarvik |
| 6,234,772 | B1 | 5/2001 | Wampler et al. |
| 6,234,998 | B1 | 5/2001 | Wampler |
| 6,245,007 | B1 | 6/2001 | Bedingham et al. |
| 6,247,892 | B1 | 6/2001 | Kazatchkov et al. |
| 6,254,359 | B1 | 7/2001 | Aber |
| 6,264,635 | B1 | 7/2001 | Wampler et al. |
| 6,293,901 | B1 | 9/2001 | Prem |
| 6,295,877 | B1 | 10/2001 | Aboul-Hosn et al. |
| 6,319,231 | B1 | 11/2001 | Andrulitis |
| 6,351,048 | B1 | 2/2002 | Schob et al. |
| 6,375,607 | B1 | 4/2002 | Prem |
| 6,422,990 | B1 | 7/2002 | Prem |
| 6,425,007 | B1 | 7/2002 | Messinger |
| 6,428,464 | B1 | 8/2002 | Bolling |
| 6,439,845 | B1 | 8/2002 | Veres |
| 6,447,266 | B2 | 9/2002 | Antaki et al. |
| 6,447,441 | B1 | 9/2002 | Yu et al. |
| 6,458,163 | B1 | 10/2002 | Slemker et al. |
| 6,508,777 | B1 | 1/2003 | Macoviak et al. |

(56) References Cited

U.S. PATENT DOCUMENTS

| | | |
|---|---|---|
| 6,508,787 B2 | 1/2003 | Erbel et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,595,762 B2 | 7/2003 | Khanwilkar et al. |
| 6,609,883 B2 | 8/2003 | Woodard et al. |
| 6,623,420 B2 | 9/2003 | Reich et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,189 B1 | 4/2004 | Jarvik et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 3/2005 | Hoover |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,027,875 B2 | 4/2006 | Siess et al. |
| 7,048,681 B2 | 5/2006 | Tsubouchi et al. |
| 7,112,903 B1 | 9/2006 | Schob |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,431,688 B2 | 10/2008 | Wampler et al. |
| 7,467,930 B2 | 12/2008 | Ozaki et al. |
| 7,470,246 B2 | 12/2008 | Mori et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,226,373 B2 | 7/2012 | Yaegashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 8,821,365 B2 * | 9/2014 | Ozaki et al. .................. 600/16 |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2004/0007515 A1 | 1/2004 | Geyer |
| 2004/0024285 A1 | 2/2004 | Muckter |
| 2004/0030381 A1 | 2/2004 | Shu |
| 2004/0210305 A1 | 10/2004 | Shu et al. |
| 2005/0089422 A1 | 4/2005 | Ozaki et al. |
| 2005/0287022 A1 | 12/2005 | Yaegashi et al. |
| 2006/0024182 A1 | 2/2006 | Akdis et al. |
| 2006/0055274 A1 | 3/2006 | Kim |
| 2007/0078293 A1 | 4/2007 | Shambaugh, Jr. |
| 2007/0134993 A1 | 6/2007 | Tamez et al. |
| 2007/0213690 A1 | 9/2007 | Phillips et al. |
| 2007/0231135 A1 | 10/2007 | Wampler et al. |
| 2007/0297923 A1 | 12/2007 | Tada |
| 2008/0021394 A1 | 1/2008 | La Rose et al. |
| 2008/0030895 A1 | 2/2008 | Obara et al. |
| 2008/0124231 A1 | 5/2008 | Yaegashi |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2011/0118766 A1 | 5/2011 | Reichenbach et al. |
| 2011/0118829 A1 | 5/2011 | Hoarau et al. |
| 2011/0129373 A1 | 6/2011 | Mori |
| 2011/0243759 A1 * | 10/2011 | Ozaki et al. .................. 417/279 |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0035411 A1 | 2/2012 | LaRose et al. |
| 2012/0078030 A1 | 3/2012 | Bourque |
| 2012/0130152 A1 * | 5/2012 | Ozaki et al. .................. 600/16 |
| 2012/0243759 A1 | 9/2012 | Fujisawa |
| 2012/0308363 A1 | 12/2012 | Ozaki et al. |
| 2013/0121821 A1 | 5/2013 | Ozaki et al. |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2014/0030122 A1 | 1/2014 | Ozaki et al. |

FOREIGN PATENT DOCUMENTS

| | | |
|---|---|---|
| EP | 1113117 A2 | 7/2001 |
| EP | 1495773 A2 | 1/2005 |
| EP | 1495773 A3 | 11/2006 |
| EP | 1495773 B1 | 2/2009 |
| EP | 2372160 A1 | 10/2011 |
| EP | 2405140 A1 | 1/2012 |
| EP | 2461465 A1 | 6/2012 |
| JP | 04/091396 A | 3/1992 |
| JP | 04/148094 A | 5/1992 |
| JP | 05/021197 U | 3/1993 |
| JP | 06/014538 U | 2/1994 |
| JP | 06/053790 U | 7/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2001-329988 A | 11/2001 |
| JP | 2003/135592 A | 5/2003 |
| JP | 2004/166401 A | 6/2004 |
| JP | 2004/209240 A | 7/2004 |
| JP | 2004/332566 A | 11/2004 |
| JP | 2004/346295 A | 12/2004 |
| JP | 2005/127222 A | 5/2005 |
| JP | 2005/270345 A | 10/2005 |
| JP | 2005/270415 A | 10/2005 |
| JP | 2005/287599 A | 10/2005 |
| JP | 2007/002885 A | 1/2007 |
| JP | 2007/043621 | 2/2007 |
| JP | 2007-89972 A | 4/2007 |
| JP | 2007/089972 A | 4/2007 |
| JP | 2007/089974 | 4/2007 |
| JP | 2007/215292 | 8/2007 |
| JP | 2007/247489 | 9/2007 |
| JP | 2008/104278 | 5/2008 |
| JP | 2008/132131 | 6/2008 |
| JP | 2008/297997 A | 12/2008 |
| JP | 2006/167173 A | 6/2009 |
| JP | 2010/136863 A | 6/2010 |
| WO | 93/07388 A1 | 4/1993 |
| WO | 96/31934 | 10/1996 |
| WO | 97/42413 A1 | 11/1997 |
| WO | 2005/028000 A1 | 3/2005 |
| WO | 2005/034312 A2 | 4/2005 |

(56) References Cited

FOREIGN PATENT DOCUMENTS

| WO | 2010/067682 A1 | 6/2010 | | |
|---|---|---|---|---|
| WO | 2010/101082 A1 | 9/2010 | | |
| WO | 2011/013483 A1 | 2/2011 | | |
| WO | WO2011/013483 A1 | 2/2011 | | |
| WO | WO2011013483 A | * | 2/2011 | ............ 600/16 |

OTHER PUBLICATIONS

European Search report Issued in European Patent Application 10/748,702.7, mailed Apr. 2, 2013.
Extended European Search Report issued in European Patent Application No. EP 10748677.1, mailed Nov. 19, 2012.
International Search Report (PCT/ISA/210) issued on Jul. 14, 2009, by Japanese Patent Office as the International Searching Authority for International Application No. PCT/JP2009/061318.
International Search Report and Written Opinion issued in PCT/JP2011/050925, mailed Apr. 12, 2011.
International Search Report and Written Opinion issued in PCT/JP2011/054134, mailed Apr. 12, 2011.
International Search Report and Written Opinion issued in PCT/JP2011/064768, mailed Sep. 13, 2011.
International Search Report and Written Opinion issued in PCT/JP2011/070450, mailed Dec. 13, 2011.
International Search Report and Written Opinion of PCT/US2014/012448 mailed on Feb. 19, 2014, 8 pages.
Kosaka, et al., "Operating Point Control System for a Continuous Flow Artificial Heart: In Vitro Study." ASAIO Journal 2003, 6 pages.
Supplementary European Search Report issued in European Application No. 09/831,786.6, dated Jan. 7, 2013, 7 pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," ASAIO Journal, 1993, 7 pages.

\* cited by examiner

FIG.28
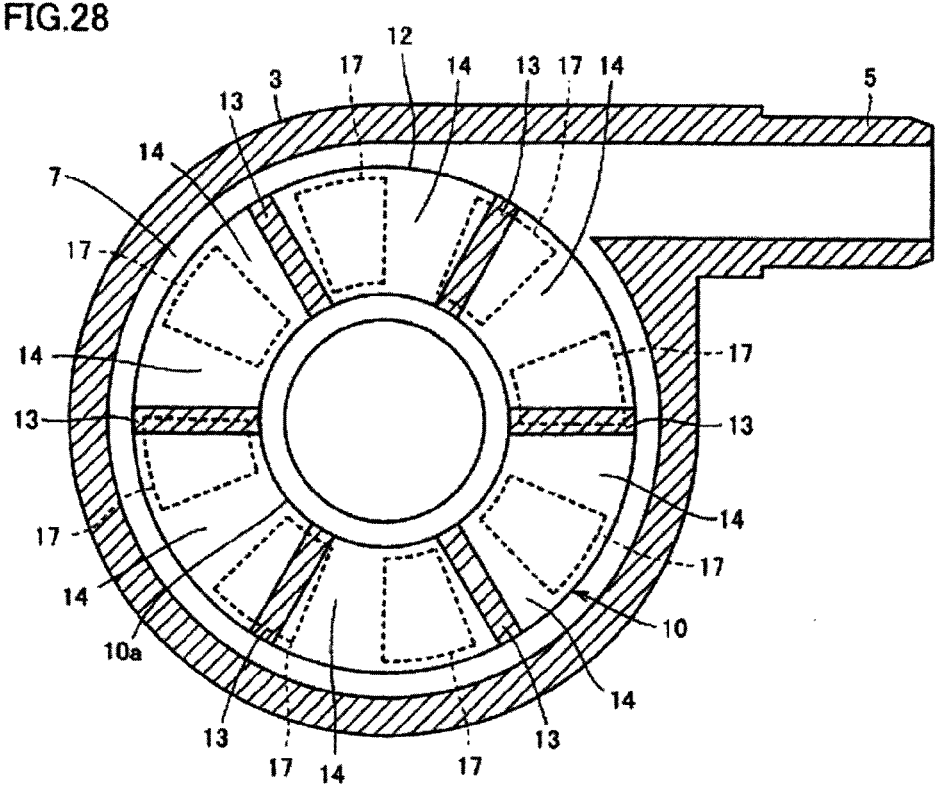
FIG.29
(a) Fourth Embodiment
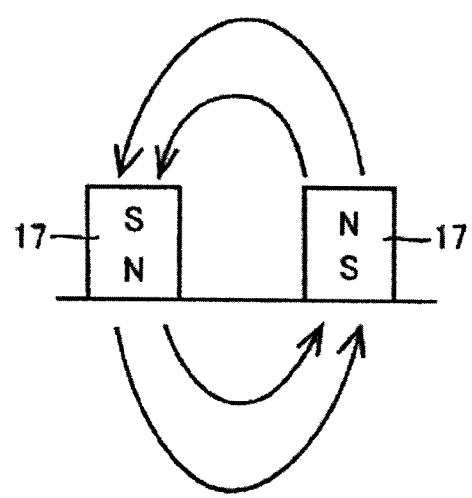
(b) First Embodiment
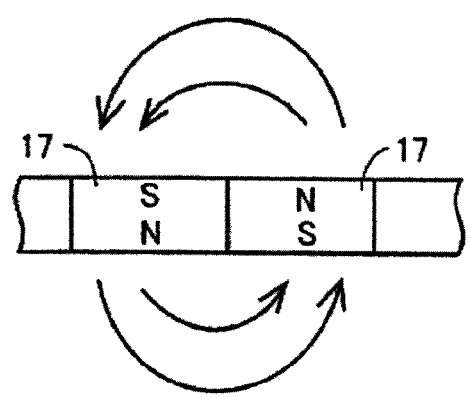

Area ratio of the permanent magnet 40 to the permanent magnet 17

FIG.32
(a)
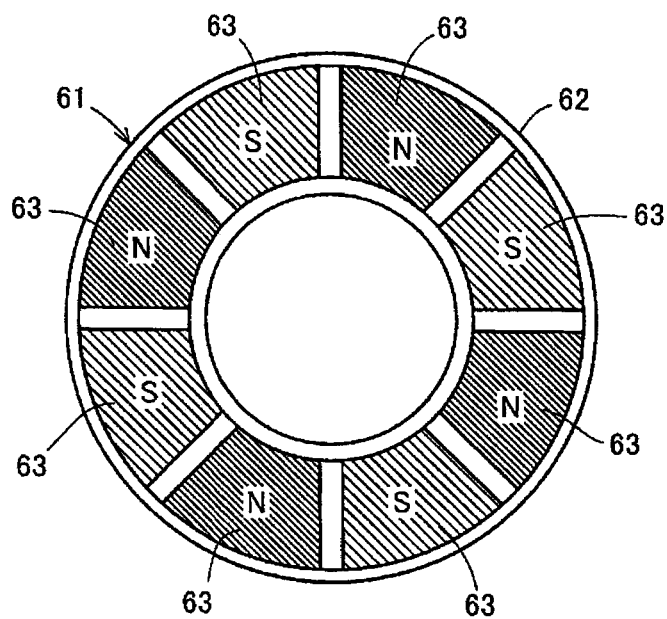
(b)
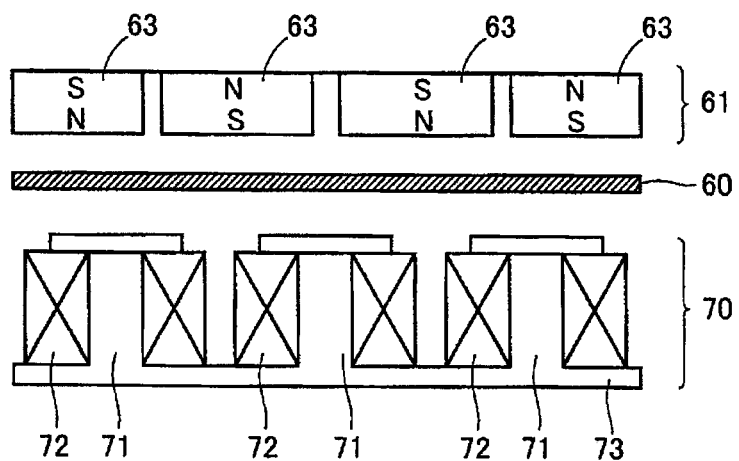

FIG.34
(a)
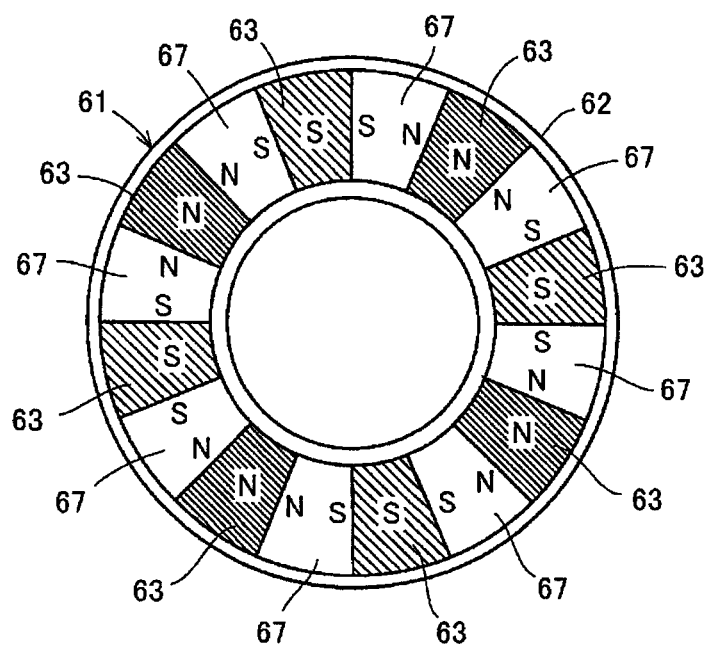
(b)
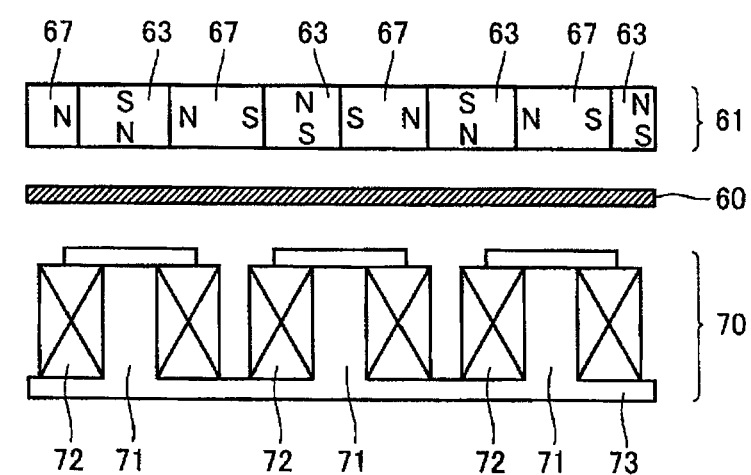

CENTRIFUGAL PUMP DEVICE

CROSS-REFERENCE TO RELATED APPLICATIONS

This application is a 35 U.S.C. §371 U.S. National Stage Entry of PCT Application Ser. No. PCT/JP2013/050187, filed on Jan. 9, 2013, that claims benefit to Japanese Patent Application No. 2012-007845, filed Jan. 18, 2012, both of are hereby incorporated by reference in their entirety.

FIELD OF THE INVENTION

The present invention relates to a centrifugal pump device, and more specifically to a centrifugal pump device provided with an impeller that sends a liquid by centrifugal force during rotation.

BACKGROUND ART

In recent years, examples that use a centrifugal blood pump device that use magnetic coupling to transmit drive torque of an external motor to an impeller within a blood chamber has increased as a blood circulation device of an artificial heart lung device. With this centrifugal blood pump device, physical communication between the blood chamber and the outside can be eliminated thereby preventing the introduction of bacteria and the like into the blood.

A centrifugal blood pump of Japanese Unexamined Patent Application Publication No. 2004-209240 (Patent Document 1) is provided with a housing including a first to a third chamber divided by first and second barrier walls, an impeller rotatably provided in the second chamber (blood chamber), a magnetic body provided on one side face of the impeller, an electrical magnet provided in the first chamber opposing one side face of the impeller, a permanent magnet provided on the other side face of the impeller, a rotor and a motor provided in the third chamber, and a permanent magnet provided on the rotor opposing the other side face of the impeller. A hydrodynamic groove is formed on the surface of the second barrier wall opposing the other side face of the impeller. The impeller separates from an inner wall of the second chamber and rotates in a non-contact state by the attractive force acting on one side face of the impeller from the electrical magnet, the attractive force acting on the other side face of the impeller from the permanent magnet of the rotor, and the hydrodynamic bearing effect of the hydrodynamic groove.

Additionally, the centrifugal blood pump of the Japanese Unexamined Patent Application Publication No. 2006-167173 (Patent Document 2) is provided with a housing including a first to a third chamber divided by first and second barrier walls, an impeller rotatably provided in the second chamber (blood chamber), a magnetic body provided on one side face of the impeller, a first permanent magnet provided in the first chamber opposing one side face of the impeller, a second permanent magnet provided on the other side face of the impeller, a rotor and a motor provided in the third chamber, and a third permanent magnet provided on the rotor opposing the other side face of the impeller. A first hydrodynamic groove is formed on the surface of the first barrier wall opposing one side face of the impeller, and a second hydrodynamic groove is formed on the surface of the second barrier wall opposing the other side face of the impeller. The impeller separates from the inner wall of the second chamber and rotates in a non-contact state by the attractive force acting on one side face of the impeller from the first permanent magnet, the attractive force acting on the other side face of the impeller from the third permanent magnet of the rotor, and the hydrodynamic bearing effect of the first and second hydrodynamic grooves.

Additionally, a turbo shaped pump in FIG. 8 and FIG. 9 of the Japanese Unexamined Patent Application Publication No. H4-91396 (Patent Document 3) is provided with a housing, an impeller rotatably provided in the housing, a first permanent magnet provided on one side face of the impeller, a rotor provided on an outer portion of the housing, a second permanent magnet provided on the rotor opposing the one side face of the impeller, a third permanent magnet provided on the other side face of the impeller, and a magnetic body provided on the housing opposing the other side face of the impeller. Additionally, the first hydrodynamic groove is formed on one side face of the impeller, and the second hydrodynamic groove is formed on other side face of the impeller. The impeller separates from the inside wall of the housing and rotates in a non-contact state by the attractive force acting on one side face of the impeller from the second permanent magnet of the rotor, the attractive force acting on the other side face of the impeller from the magnetic body of the housing, and the hydrodynamic bearing effect of the first and second hydrodynamic grooves.

Furthermore, a clean pump of the Japanese Unexamined Utility Model Application Publication No. H6-53790 (Patent Document 4) is provided with a casing, an impeller rotatably provided in the casing, a first permanent magnet provided on one side face of the impeller, a rotor provided on an outer portion of the casing, a second permanent magnet provided on the rotor opposing one side face of the impeller, a magnetic body provided on the other side face of the impeller, and an electrical magnet provided outside the housing opposing the other side face of the impeller. Additionally, the hydrodynamic groove is formed on one side face of the impeller.

When the rotational speed of the impeller is lower than a predetermined rotational speed, the electrical magnet activates, and when the rotational speed of the impeller exceeds a predetermined rotational speed, the power distribution to the electrical magnet is stopped. The impeller separates from the inside wall of the housing and rotates in a non-contact state by the attractive force acting on one side face of the impeller from the second permanent magnet of the rotor, and the hydrodynamic bearing effect of the hydrodynamic groove.

RELATED ART DOCUMENTS

Patent Documents

Patent Document 1: Japanese Unexamined Patent Application Publication No. 2004-209240
Patent Document 2: Japanese Unexamined Patent Application Publication No. 2006-167173
Patent Document 3: Japanese Unexamined Patent Application Publication No. H4-91396
Patent Document 4: Japanese Unexamined Utility Model Application Publication No. H6-53790

SUMMARY OF THE INVENTION

Problems to be Solved by the Invention

The pumps in the above Patent Documents 1 to 4, are common with respect to supporting the impeller in an axial direction by the hydrodynamic groove formed in the impeller and in the opposing portion of the housing, and supporting the impeller in a radial direction by the attractive force of the permanent magnet provided outside the housing and by the permanent magnet provided on the impeller.

The support rigidity of the hydrodynamic groove is proportional to the rotational speed of the impeller. Therefore, in order to stabilize and rotate the impeller without contacting the housing, even in a state when interference is applied to the pump, increasing the normal rotational speed range of the pump and raising the rigidity of the axial direction of the impeller is necessary. However, in the pump of the above Patent Documents 1 to 4, the radial direction is supported using the attractive force of the permanent magnet, therefore, there is a problem in that that support rigidity is low and the impeller cannot be rotated at a high speed.

As a method of increasing the rigidity of this radial direction, there is a method for strengthening the attractive forces of the permanent magnet in the impeller and the permanent magnet or a stator distributed on the outer portion of the housing. However, if that attractive force is strengthened, there is a problem in that the negative rigidity value in the axial direction of the impeller becomes larger (namely, if the impeller moves in the axial direction, that attractive force becomes larger to the extent of the movement), the support capability of the impeller by hydrodynamics and the attractive force acting on the impeller housing becomes larger, and a smooth rotation drive of the impeller becomes difficult.

In particular, as illustrated in FIG. 39 of Patent Document 2, when the impeller is rotated with magnetic interaction of the permanent magnet distributed to the motor coil and the impeller, the starting torque is small compared to when the impeller illustrated in FIG. 3 of Patent Document 2 is rotatably driven with magnetic coupling between permanent magnets, therefore, a smooth rotary drive of the impeller is difficult.

In order to handle this, a method has been proposed in Patent Document 2 that an electrical magnet to bias the impeller in a predetermined direction, or a magnetic force adjusting coil to change the magnetic force of the permanent magnet, is provided, these are activated at the start rotation of the impeller, and the start of the impeller is smooth. However, in this type of handling method, there is a problem in that the pump size becomes larger from the fact that new exclusive-use members such as an electrical magnet or a coil is necessary, and reliability decreases as the number of components increase. These problems are critical to a blood pump used in an artificial heart and the like.

Therefore, a main object of this invention is to provide a small centrifugal pump device that can turn an impeller at a high speed and that can start rotation of an impeller smoothly.

Means for Solving the Problem

The centrifugal pump device according to this invention is provided with a housing including a first and a second chamber divided by a barrier wall; an impeller rotatably provided along the barrier wall in the first chamber that sends a liquid by centrifugal force at the time of rotation, and a drive portion provided in the second chamber that rotatably drives the impeller with the barrier wall there between, and includes a first magnetic body provided on one side face of the impeller, a second magnetic body provided on an inner wall of the first chamber opposing one side face of the impeller that attracts the first magnetic body, and a plurality of first permanent magnets provided the other side face of the impeller arranged along a same circle such that adjacent magnetic poles are mutually different. The drive portion includes a plurality of a third magnetic bodies provided opposing the plurality of first permanent magnets forming a cylindrical shape, respectively, and a plurality of coils provided corresponding to each of the plurality of third magnetic bodies wound around each corresponding third magnetic body to generate a rotating magnetic field. A first attractive force between the first and second magnetic bodies and a second attractive force between the plurality of first permanent magnets and the plurality of third magnetic bodies are balanced in a substantial center of a range of movement of the impeller in the first chamber during rotation of the impeller. A first hydrodynamic groove is formed on one side face of the impeller or on an inner wall of the first chamber facing thereto, and a second hydrodynamic groove is formed on the other side face of the impeller or on the barrier wall facing thereto.

Therefore, a third magnetic body is provided within each coil of the drive unit, and because this third magnetic body and the first permanent magnet of the impeller are magnetically coupled, the impeller can rotate at a high speed by adjusting the coil electric current, and the start rotation force of the impeller can become larger while maintaining the small shape of the pump size.

Additionally, a large space for the coil can be ensured and the number of turns in a coil can be made larger because the third magnetic body is formed in a cylindrical shape. Therefore, a large torque for rotatably driving the impeller is generated. Additionally, the copper loss generated in the motor coil can be reduced and the energy efficiency in the rotary drive of the impeller can be increased.

Note that, the cross sectional shape of the third magnetic body cut in a perpendicular plane in the axial direction is not limited to a perfect circle, but may be an elliptical shape with an ellipicity (=minor axis/major axis) of 0.5 or more. In such a case, the coil can be easily wound, and a large space for the coil can be ensured because there is no corner portion on the outer peripheral surface of the third magnetic body. The ellipicity of the third magnetic body is determined according to the dimensions of the inner and outer diameters of the space for the coil and by the slot number of the motor.

Alternatively, the drive unit further includes a fourth magnetic body provided on a tip end surface opposing the first permanent magnet of the third magnetic body. An area of a surface opposing the first permanent magnet of the fourth magnetic body is larger than an area of a tip end surface of the third magnetic body. In this case, the attractive force of the first permanent magnet and the drive unit can become larger, and the energy efficiency in the rotary drive of the impeller can be increased.

In addition, preferably, the mutually opposing surfaces of each adjacent two fourth magnetic bodies are further provided substantially parallel. In this case, a large torque for rotatably driving the impeller can be generated.

In addition, preferably, each third magnetic body includes a plurality of steel plates stacked in the length direction of the rotational axis of the impeller. In this case, the eddy-current loss generated in the third magnetic body can be reduced and the energy efficiency in the rotary drive of the impeller can be increased.

In addition, preferably, each third magnetic body includes a plurality of steel plates stacked in the rotational direction of the impeller. In this case, the eddy-current loss generated in the third magnetic body can be reduced and the energy efficiency in the rotary drive of the impeller can be increased.

In addition, preferably, each third magnetic body includes a plurality of steel plates stacked in the diameter direction of the impeller. In this case, the eddy-current loss generated in the third magnetic body can be reduced and the energy efficiency in the rotary drive of the impeller can be increased.

In addition, preferably, each third magnetic body is formed by powder of pure iron, soft iron, or ferrosilicon. In this case, the iron loss in the third magnetic body can be reduced and the energy efficiency in the rotary drive of the impeller can be increased.

In addition, preferably, each of the first and second magnetic bodies is a permanent magnet. In addition, preferably, a plurality of second permanent magnets is further provided on the other side face of the impeller inserted into a plurality of gaps in a respective plurality of first permanent magnets. Each second permanent magnet is magnetized in the rotational direction of the impeller. A first magnetic pole of each second permanent magnet faces the first permanent magnet side where a first magnetic pole is faced to the barrier wall side of two adjacent first permanent magnets. A second magnetic pole of each second permanent magnet faces the first permanent magnet side where a second magnetic pole is faced to the barrier wall side of two adjacent first permanent magnets. Employing this type of Halbach array, even when the gap between the first permanent magnet and the third magnetic body is large, the field magnetic flux of the first permanent magnet can be spread through the motor stator efficiently, and a large torque for rotatably driving the impeller can be generated.

In addition, preferably, the sum of the absolute value of the negative support rigidity value in the axial direction of the impeller configured by first and second attractive forces, and the absolute value of the positive rigidity value in the radial direction of the impeller is smaller than the absolute value of the positive rigidity value obtained in the first and second hydrodynamic grooves in the normal rotational speed range that rotates the impeller.

In addition, preferably, the hydrodynamic force generated by the first hydrodynamic groove and the hydrodynamic force generated by the second hydrodynamic groove are different.

In addition, preferably, at least one of either the first or second hydrodynamic grooves is an inward spiral groove.

In addition, preferably, a diamond-like carbon film for decreasing the frictional force on at least one of either the surface of the impeller or the inner wall of the first chamber is formed.

In addition, preferably, the liquid is blood and the centrifugal pump device is used for circulating the liquid. In this case, the impeller starts rotation smoothly, and the generation of hemolysis can be prevented because the distance between the impeller and the housing is ensured.

Effect of the Invention

As described above, according to this invention, the impeller can be rotated at a high speed, and the start rotation force of the impeller can become larger while maintaining the small shape of the pump size. Additionally, the mechanical contact of the impeller and the housing can become less, and the impeller can stably emerge. Additionally, the liquid can be drained smoothly. Additionally, the impeller can start rotating smoothly. Additionally, a large torque for rotatably driving the impeller is generated. Additionally, the energy efficiency in the rotation drive of the impeller can be increased. Additionally, when circulating the blood, hemolysis can be avoided.

BRIEF DESCRIPTION OF THE DRAWINGS

FIG. 28 is a cross sectional view illustrating the main sections of the centrifugal blood pump device according to the fourth embodiment of this invention.

FIG. 29 is a drawing for describing an effect of the fourth embodiment.

FIG. 32 is a drawing illustrating the configuration of the axial gap type motor according to the fifth embodiment of this invention.

FIG. 34 is a drawing illustrating an alternative example of the fifth embodiment.

MODE FOR CARRYING OUT THE INVENTION

[First Embodiment]

Figure 1:
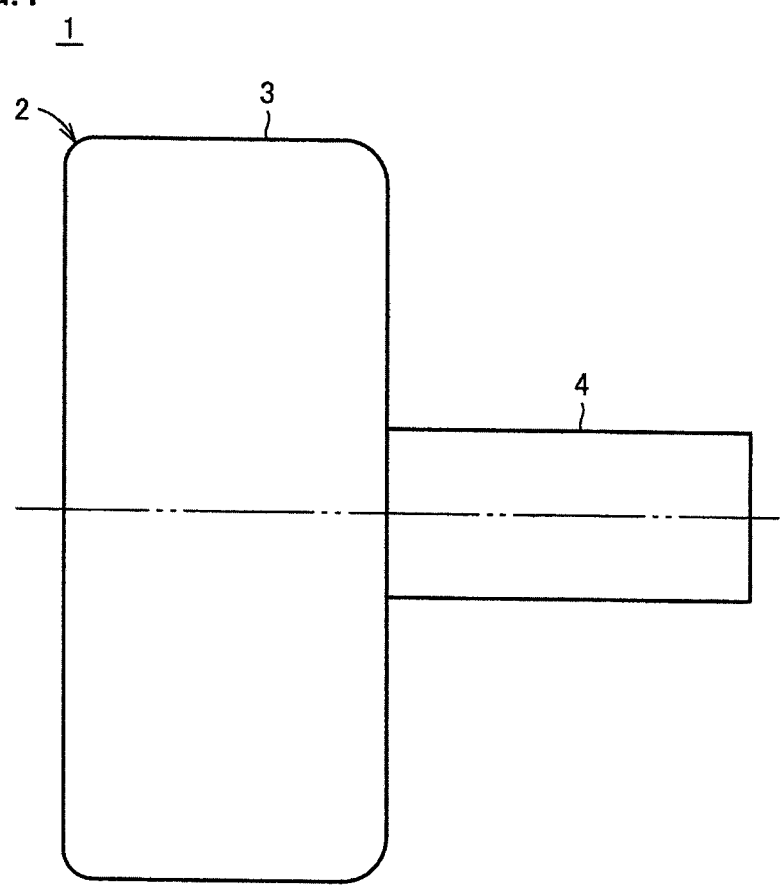
FIG. 1 is a front view illustrating the exterior of the pump portion of the centrifugal blood pump device according to the first embodiment of this invention.
Figure 2:
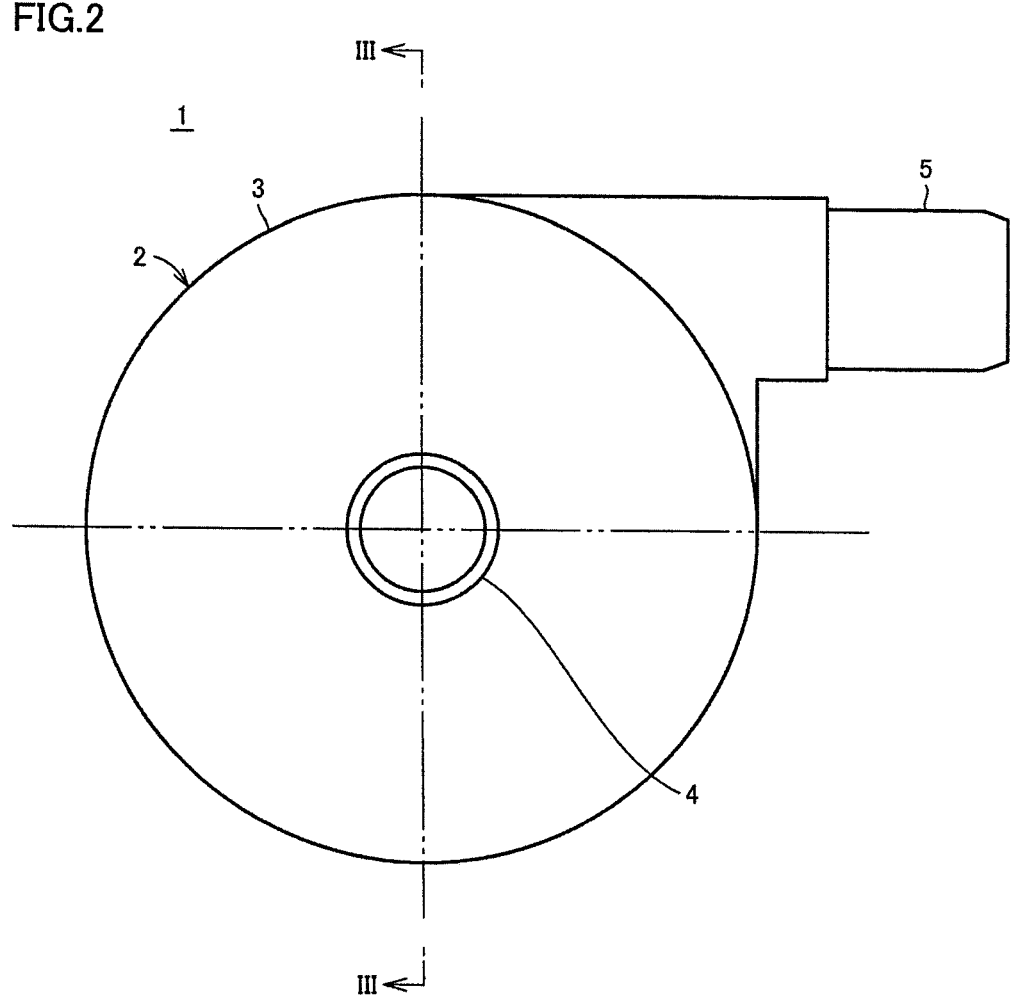
FIG. 2 is a side view of the pump portion illustrated in FIG. 1.
Figure 3:
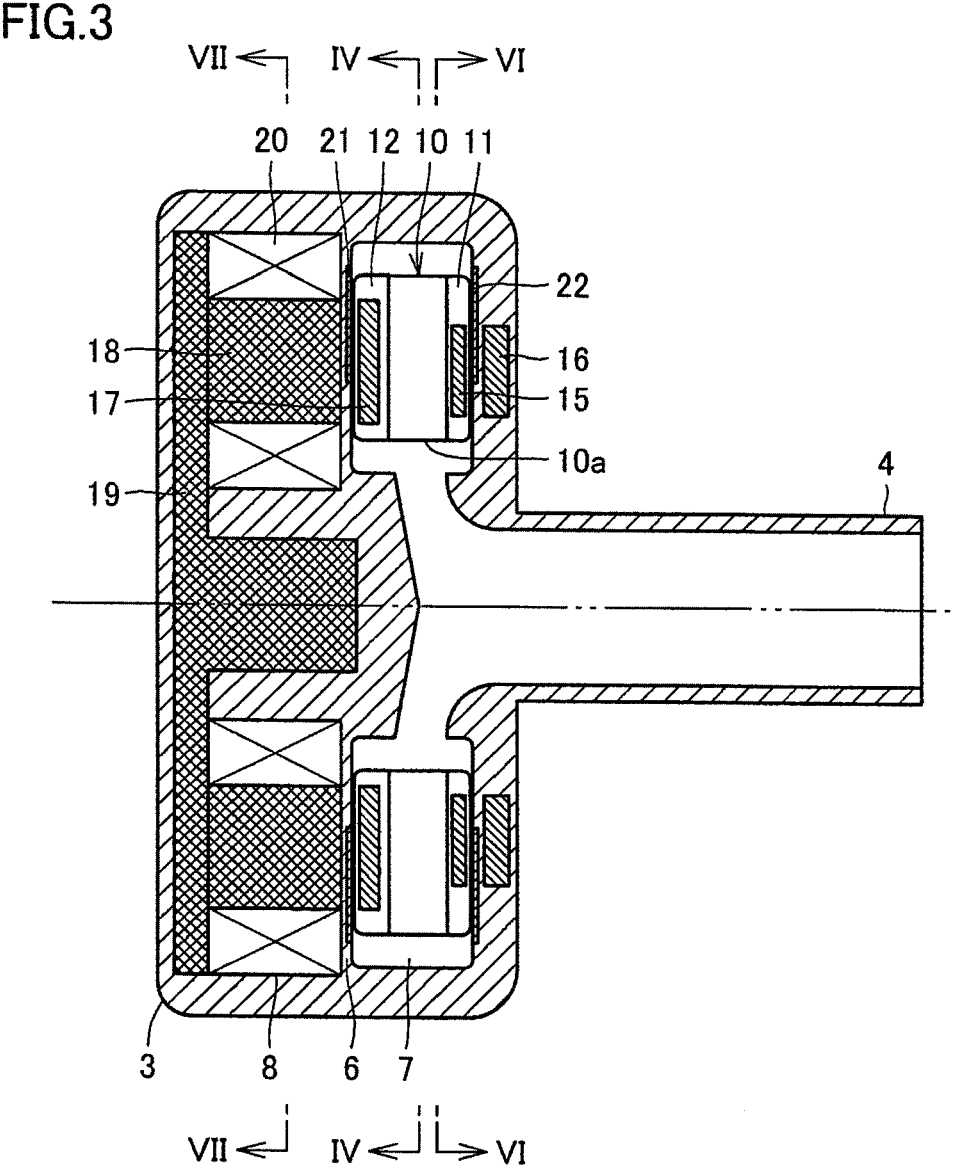
FIG. 3 is a cross sectional view of the line in FIG. 2.
Figure 4:
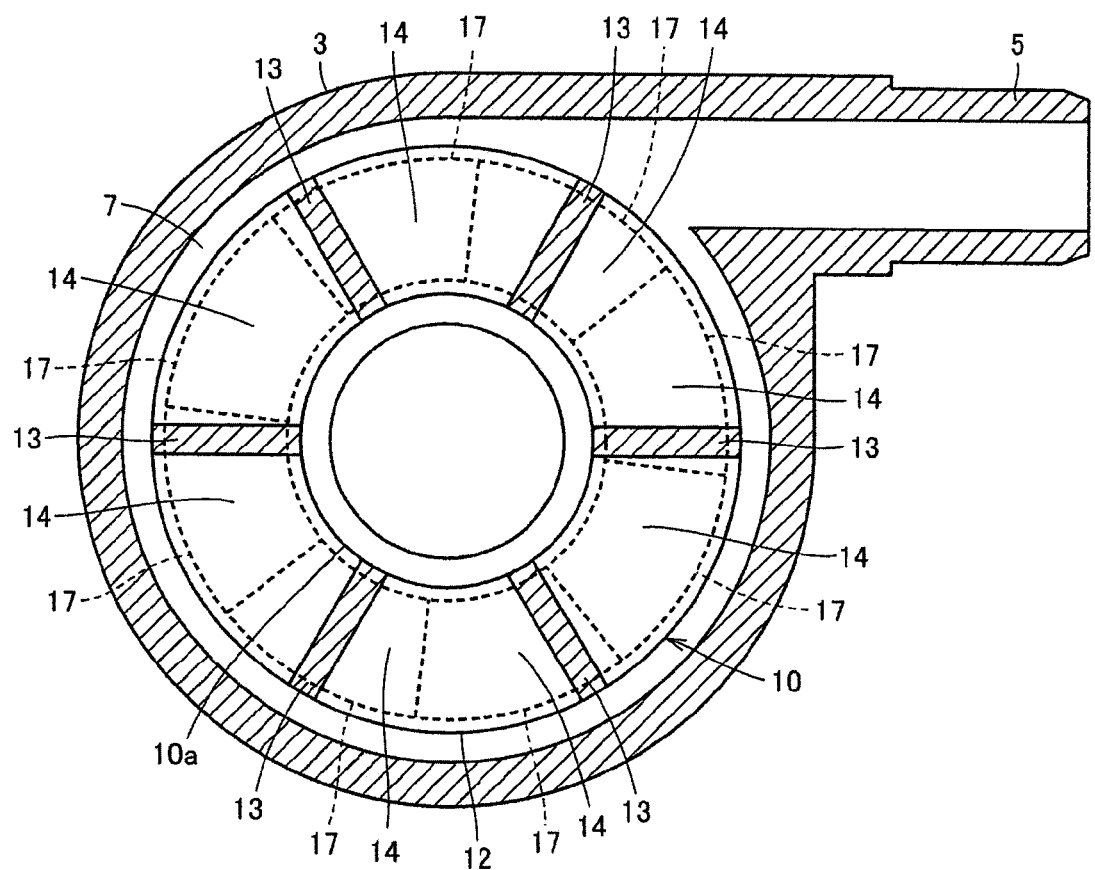
FIG. 4 is a cross sectional view of the IV-IV line in FIG. 3.
Figure 5:
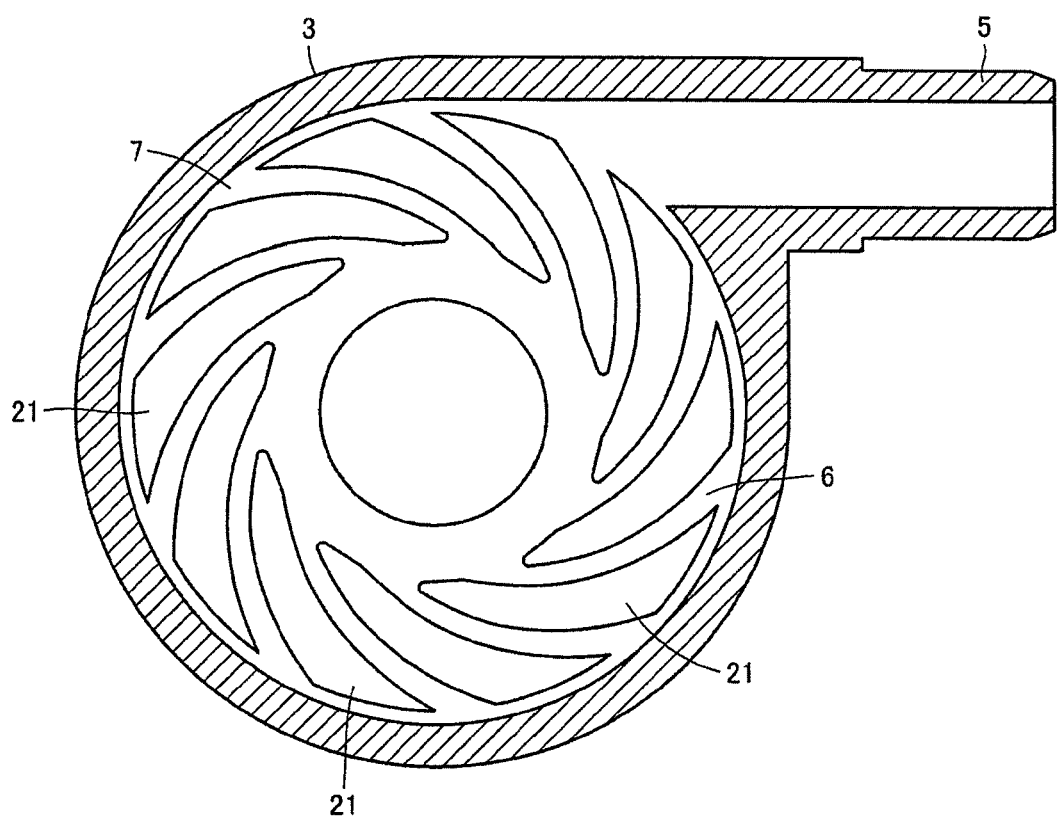
FIG. 5 is a cross sectional view illustrating the state of releasing the impeller from the cross sectional view of the IV-IV line in FIG. 3.
Figure 6:
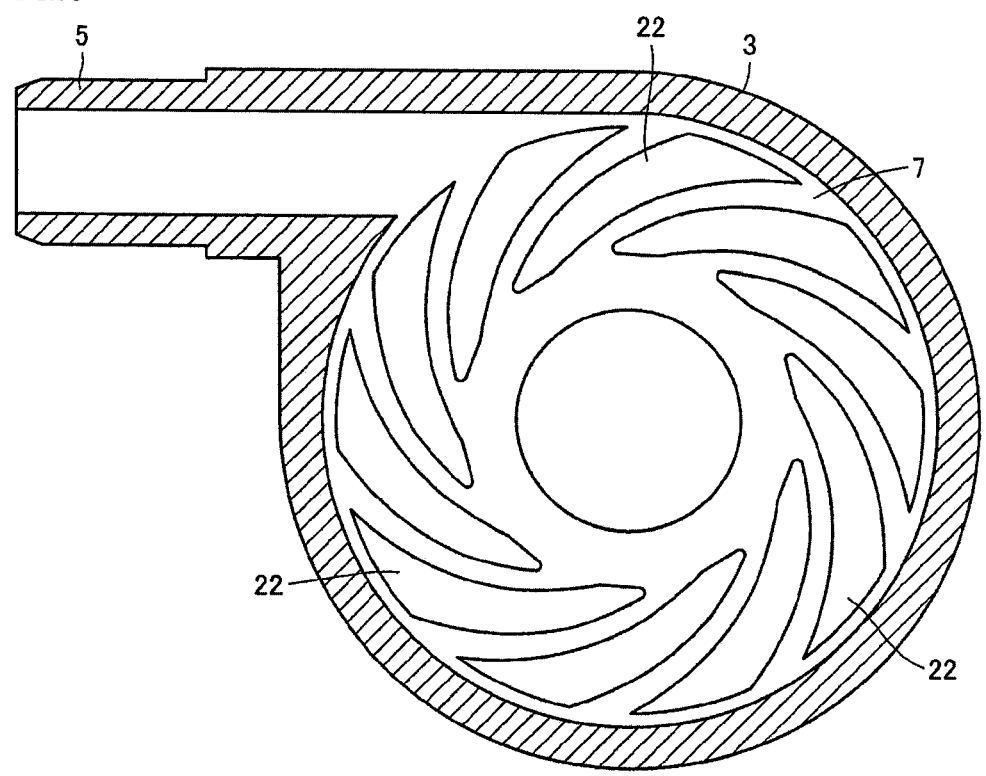
FIG. 6 is a cross sectional view illustrating the state of releasing the impeller from the cross sectional view of the VI-VI line in FIG. 3.
Figure 7:
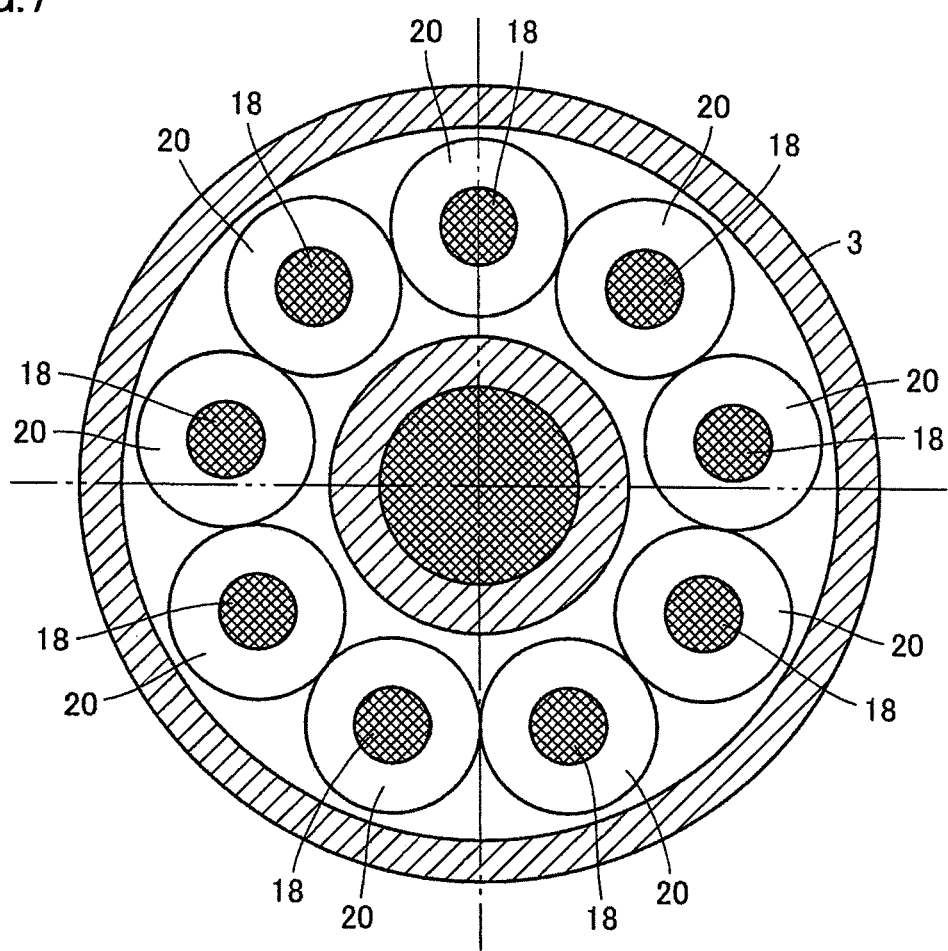
FIG. 7 is a cross sectional view of the VII-VII line in FIG. 3.

FIG. 1 is a front view illustrating the exterior of the pump portion 1 of the centrifugal blood pump device according to the first embodiment of this invention, and FIG. 2 is a side view thereof. FIG. 3 is a cross sectional view of line in FIG. 2, FIG. 4 is a cross sectional view of the IV-IV line in FIG. 3, and FIG. 5 is a cross sectional view illustrating the state of releasing the impeller from the cross sectional view of the VI-VI line in FIG. 3. FIG. 6 is a cross sectional view illustrating the state of releasing the impeller from the cross sectional view of the VI-VI line in FIG. 3, and FIG. 7 is a cross sectional view of the VII-VII line in FIG. 3.

In FIG. 1 to FIG. 7, a pump portion 1 of this centrifugal blood pump device is provided with a housing 2 formed with nonmagnetic material. A housing 2 includes a cylindrical shape main body 3, a cylindrical blood inflow port 4 erected in the middle of the end face of one side of the main body 3, and a cylindrical blood inflow port 5 provided on the outer periphery of the main body 3. The blood outflow port 5 is extended in the tangential direction of the outer periphery of the main body 3.

A blood chamber 7 divided by a barrier wall 6 as illustrated in FIG. 3 and a motor chamber 8 are provided within the housing 2. A disk-shaped impeller 10 having a through-hole 10a in the center is rotatably provided, as illustrated in FIG. 3 and FIG. 4, within the blood chamber 7. The impeller 10 includes a plurality of (six, for example) vanes 13s formed between two doughnut board shaped shrouds 11,12 and two shrouds 11, 12. The shroud 11 is disposed on the blood inflow port 4 side, and the shroud 12 is disposed on the barrier wall 6 side. The shroud 11, 12 and the vane 13 are formed with nonmagnetic material.

A plurality of (6, in this case) blood passages 14 divided by a plurality of panes 13 are formed between the two shrouds 11, 12. The blood passage 14 communicates with the through-hole 10a in the middle of the impeller 10, and extends to enable the width to gradually spread to the outer periphery, with the through-hole 10a of the impeller 10 as the beginning, as illustrated in FIG. 4. That is to say, the vane 13 is formed between the two adjacent blood passages 14. Note that, in this first embodiment, a plurality of vanes 13 are provided at equal angular intervals, and formed in the same shape. Therefore, a plurality of blood passages 14 are provided at equal angular intervals, and formed in the same shape.

When the impeller 10 rotatably drives, the blood that inflows from the blood inflow port 4 is sent to the outer perimeter of the impeller 10 through the blood passage 14 from the through-hole 10a by a centrifugal force, and outflows from the blood outflow port 5.

Additionally, a permanent magnet 15 is embedded in the shroud 11, and a permanent magnet 16 that attracts the permanent magnet 15 is embedded in the inner wall of the blood chamber 7 opposing the shroud 11. The permanent magnets 15, 16 are provided for attracting (that is to say, energizing) the impeller 10 to the motor chamber 8 and the opposite side, that is to say the blood inflow port 4 side.

Note that, a permanent magnet can be provided on one side of the inner wall of the shroud 11 and the blood chamber 7 instead of providing the permanent magnets 15, 16 on the inner wall of the shroud 11 and the blood chamber 7, respectively, and a magnetic body can be provided on the other side. Additionally, the shroud 11 itself can be formed with the permanent magnet 15 or a magnetic body. Moreover, either a soft magnetic body or a hard magnetic body can be used for a magnetic body.

Additionally, there can be one or a plurality of permanent magnets 16. If there is one permanent magnet 16, the permanent magnet 16 is formed in a ring shape. Moreover, if there are a plurality of permanent magnets 16, the plurality of permanent magnets 16 are disposed along the same circle at equal angular intervals. The same goes for the permanent magnet 15 as the permanent magnet 16; there can be one or a plurality of permanent magnets.

Additionally, a plurality of (8, for example) permanent magnets 17 are embedded in the shroud 12, as illustrated in FIG. 4. The plurality of permanent magnets 17 are disposed along the same circle at equal angular intervals so that adjacent magnetic poles are mutually different. That is to say, the permanent magnet 17 in which the N pole faces the motor chamber 8 side and the permanent magnet 17 in which the S pole faces the motor chamber 8 side are disposed alternately along the same circle at equal angular intervals.

Additionally, a plurality of (9, for example) magnetic bodies 18 are provided in the motor chamber 8, as illustrated in FIG. 7. The plurality of magnetic bodies 18 oppose the plurality of permanent magnets 17 of the impeller 10 and are disposed along the same circle at equal angular intervals. The base end of the plurality of magnetic bodies 18 are coupled to one disk-shaped yoke 19. A coil 20 is wound around each magnetic body 18.

Here, each of the plurality of magnetic bodies 18 are formed in a circular cylindrical shape and the plurality of magnetic bodies 18 have the same dimensions as each other. The end face of the base end side of the circular cylindrical shaped magnetic body 18 is coupled to the yoke 19, and the end face of the tip side is opposing the plurality of permanent magnets 17 of the impeller 10 through the barrier wall 6. Additionally, space for winding the coil 20 is equally ensured in the surrounding area of the plurality of magnetic bodies 18.

Generally, in an axial gap type motor, the magnetic body 18 is commonly made in a triangular prism shape or a fan-shaped shape. This is because providing these types of shapes allows the mutually opposing surfaces of the two adjacent magnetic bodies 18 easily made to be substantially parallel, and prevents the adjacent coils 20 from interfering with each other and decreasing the winding capacity.

However, when considering the motor efficiency, having the magnetic body 18 in a circular cylindrical shape is preferred. For example, when the coil 20 is wound the same number of times around the triangular prism shaped magnetic body 18 and the circular cylindrical shaped magnetic body 18, respectively, the wound circular cylindrical shaped magnetic body 18 can shorten the length of the leading wires of the coil 20, and can decrease the resistance value of the coil 20. In other words, the copper loss generated in the coil 20 can be reduced and the energy efficiency in the rotation drive of the impeller 10 can be increased.

Note that, the outer surface surrounding the plurality of permanent magnets 18 (the circle surrounding the periphery of the plurality of permanent magnets 18 in FIG. 7) can match the outer surface surrounding the plurality of permanent magnets 17 (the circle surrounding the periphery of the plurality of permanent magnets 17 in FIG. 4) or the outer surface surrounding the plurality of permanent magnets 18 can be larger than the outer surface surrounding the plurality of permanent magnets 17. Additionally, in the maximum rating (condition for when the rotation drive torque of the impeller 10 is at maximum) of the pump 1, the magnetic body 18 is preferably designed not to be magnetically saturated.

Figure 8:
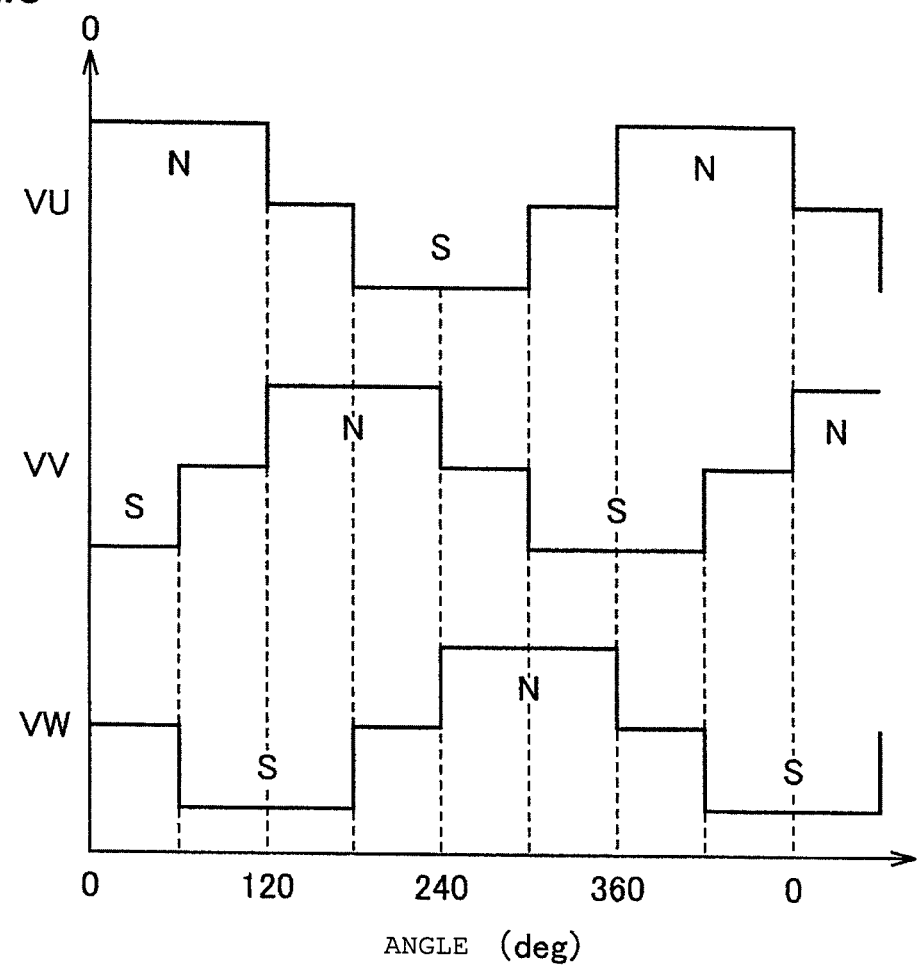
FIG. 8 is a time chart exemplifying the voltage applied to the plurality of coils illustrated in FIG. 7.

Voltage is applied with a 120 degree power distribution formula, for example, to nine coils 20. Namely, the nine coils 20 are made into groups of three. Voltages VU, VV, and VW, as illustrated in FIG. 8, are applied to the coil 20 of each group 1 to 3. In the first coil 20, positive voltage is applied to the period of 0 to 120 degrees, 0V is applied to the period of 120 to 180 degrees, negative voltage is applied to the period of 180 to 300 degrees, and 0V is applied to the period of 300 to 360 degrees. Therefore, the tip end surface of the magnetic body 18 that the first coil 20 is wound around (the end face of the impeller 10 side) is the N pole in the period of 0 to 120 degrees and the S pole in the period of 180 to 300 degrees. The phase of voltage VV is 120 degrees slower than the voltage VU, and the phase of voltage VW is 120 degrees slower than the voltage VV. Therefore, the rotating field can be formed by applying voltage VU, VV, VW to the first to third coils 20, respectively, and the impeller 10 can be rotated by the attractive force and repulsive force with the plurality of magnetic bodies 18 and the plurality of permanent magnets 17 of the impeller 10.

Here, when the impeller 10 is rotating at the rated rotational speed, the attractive force between the permanent magnets 15, 16 and the attractive force between the plurality of permanent magnets 17 and the plurality of magnetic bodies 18 balance out in the vicinity of the substantial center of the range of movement of the impeller 10 within the blood chamber 7. For this reason, the acting force from the attractive force of the impeller 10 in any range of movement of the impeller 10 is incredibly small. As a result, the friction resistance during relative slipping between the impeller 10 and housing 2 generated at the start rotation of the impeller 10 can become smaller. Additionally, there is no damage of the surface (roughness of the surface) of the inner wall of the impeller 10 and the housing 2 during relative slipping, and furthermore, when the hydrodynamic force at the time of slow speed rotation is small, the impeller 10 easily emerges from the housing 2 and becomes a non-contact state. Therefore, hemolysis or blood clotting occurring due to relative slipping between the impeller 10 and the housing 2, and blood clot occurring due marginal surface damage (roughness) generated during relative slipping, does not occur.

Additionally, a plurality of hydrodynamic grooves 21 are formed on the surface of a barrier wall 6 opposing the shroud 12 of the impeller 10, and a plurality of hydrodynamic grooves 22 are formed on the inner wall of the blood chamber 7 opposing the shroud 11. A hydrodynamic bearing effect is generated between each of the hydrodynamic grooves 21, 22 and the impeller 10 if the rotation speed of the impeller 10 exceeds the predetermined rotational speed. From this, a drag relative to the impeller 10 from each of the hydrodynamic grooves 21, 22 is generated, and the impeller 10 rotates in a non-contact state within the blood chamber 7.

More specifically, the plurality of hydrodynamic grooves 21 are formed to correspond with the size of the shroud 12 of the impeller 10, as illustrated in FIG. 5. Each hydrodynamic groove 21 has one end on the periphery (circumference) of the circular portion slightly separated from the center of the barrier wall 6, and extends to enable the width to gradually spread to the vicinity of the outer rim of the barrier wall 6 in a spiraling shape (that is to say, curved). Additionally, the plurality of hydrodynamic grooves 21 are the same shape and are disposed with the same spacing. The hydrodynamic groove 21 is a concave portion, and the depth of the hydrodynamic groove 21 is preferably about 0.0005 to 0.4 mm. The number of hydrodynamic grooves 21 is preferably about 6 to 36.

In FIG. 5, ten of the hydrodynamic grooves 21 are disposed at the same angle relative to the center axis of the impeller 10. The pressure of the liquid toward the inner diameter portion from the outer diameter portion of the hydrodynamic groove 21 increases when the impeller 10 rotates in a clock-wise direction because the hydrodynamic groove 21 is a so-called inward spiral groove. For this reason, a repulsive force is generated between the impeller 10 and the barrier wall 6, and this becomes the hydrodynamic force.

Note that, the hydrodynamic grooves 21 may be provided on the surface of the shroud 12 of the impeller 10 instead of providing the hydrodynamic grooves 21 on the barrier wall 6.

In this manner, the impeller 10 separates from the barrier wall 6, and rotates in a non-contact state by the hydrodynamic bearing effect formed between the impeller 10 and the plurality of hydrodynamic grooves 21. For this reason, a blood flow passage between the impeller 10 and the barrier wall 6 is ensured, and the pooling of blood and the occurrence of blood clotting that is attributed between both sides is prevented. Furthermore, in a normal state the occurrence of partial blood clotting between both sides can be prevented because the hydrodynamic groove 21 exerts the mixing action between the impeller 10 and the barrier wall 6.

Additionally, the corner portion of the hydrodynamic groove 21 is preferably rounded to hold at least 0.05 mm or more of R. From this, the generation of hydrolysis can be made less.

Additionally, the plurality of hydrodynamic grooves 22 are formed to correspond with the size of the shroud 11 of the impeller 10, which is the same as the plurality of hydrodynamic grooves 21, as illustrated in FIG. 6. Each hydrodynamic groove 22 has one end on the periphery (circumference) of the circular portion slightly separated from the center of the inner wall of the blood chamber 7, and extends to enable the width to gradually spread to the vicinity of the outer rim of the inner wall of the blood chamber 7 in a spiraling shape (that is to say, curved). Additionally, the plurality of hydrodynamic grooves 22 are the same shape and are disposed in the same spacing. The hydrodynamic groove 22 is a concave portion, and the depth of the hydrodynamic groove 22 is preferably about 0.005 to 0.4 mm. The number of hydrodynamic grooves 22 is preferably about 6 to 36. In FIG. 6, ten of the hydrodynamic grooves 22 are disposed at the same angle relative to the center axis of the impeller 10.

Note that, the hydrodynamic groove 22 may be provided on the surface of the shroud 11 of the impeller 10 and not on the inner wall side of the blood chamber 7. Additionally, the portion which becomes the corner of the hydrodynamic groove 22 is preferably rounded to hold at least 0.05 mm or more of R. From this, the generation of hydrolysis can be made less.

In this manner, the impeller 10 separates from the inner wall of the blood chamber 7, and rotates in a non-contact state by the hydrodynamic bearing effect formed between the impeller 10 and the plurality of hydrodynamic grooves 22. Additionally, adhesion to the inner wall of the blood chamber 7 of the impeller 10 can be prevented when the pump portion 1 receives an outside shock or when there is an excess of hydrodynamic force from the hydrodynamic groove 21. The hydrodynamic force generated by the hydrodynamic groove 21 and the hydrodynamic force generated by the hydrodynamic groove 22 may be different.

It is preferred that the impeller 10 rotate in substantially the same state in the gap between the barrier wall 6 and the shroud 12 of the impeller 10 and the gap between the inner wall of the blood chamber 7 and the shroud 11 of the impeller 10. When there is significant interference to the fluid force and the like operating in the impeller 10, and one of the gaps becomes narrow, it is preferred to make the hydrodynamic force from the hydrodynamic groove of that side that becomes narrow larger than the hydrodynamic force from the other hydrodynamic groove, and make the shape of the hydrodynamic grooves 21 and 22 different in order to make both gaps the same.

Note that, in FIG. 5 and FIG. 6, each of the hydrodynamic grooves 21, 22 are shaped in an inward spiral groove, but other shaped hydrodynamic grooves 21, 22 may be used. However, when circulating the blood, employing the inward spiral groove shaped hydrodynamic grooves 21, 22 that can drain the blood smoothly is preferred.

Figure 9:
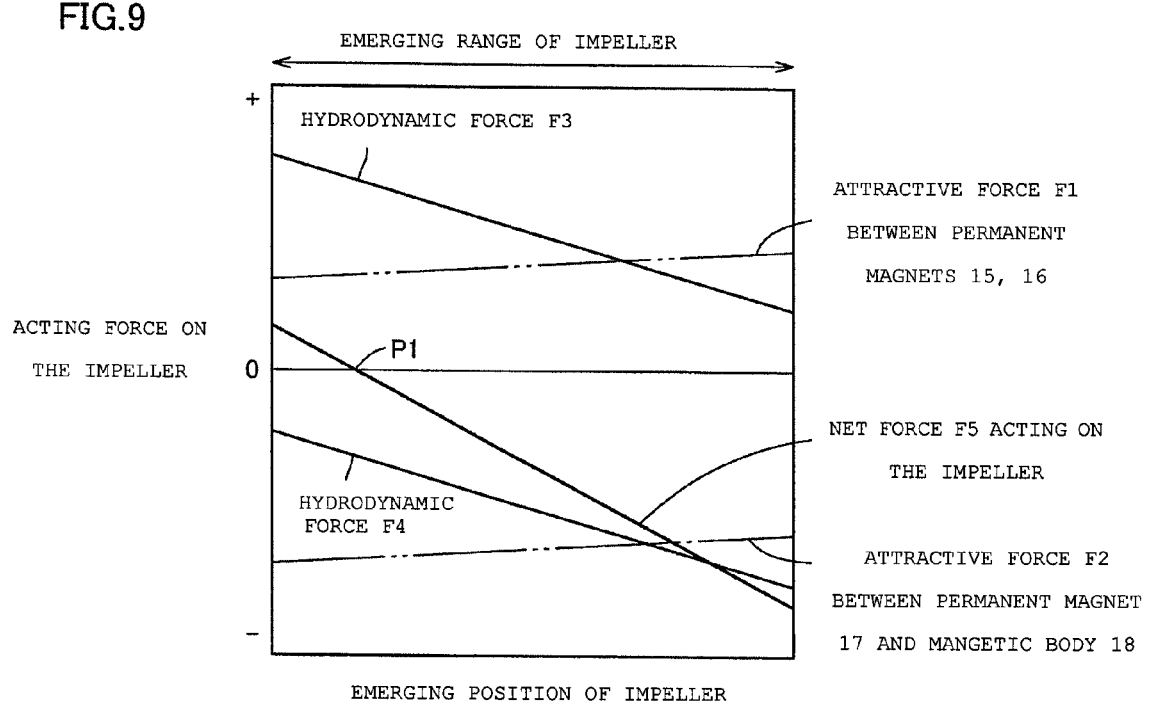
FIG. 9 is a drawing for describing an effect of the present invention.

FIG. 9 is a drawing illustrating the force acting on the impeller 10 when the magnitude of the total force of an attractive force F1 between the permanent magnets 15, 16 and an attractive force F2 between the permanent magnet 17 and the magnetic body 18 is adjusted to be zero at a position pl of everywhere but the middle position of the range of movement within the blood chamber 7 of the impeller 10. However, the rotational speed of the impeller 10 is maintained at the rated value.

Namely, the attractive force F1 between the permanent magnets 15, 16 is set smaller than the attractive force F2 between the permanent magnet 17 and the magnetic body 18, and the emerging position of the impeller 10 when the total force of those is zero is more to the barrier wall 6 side than in the middle of the impeller range of movement. The shape of the hydrodynamic grooves 21, 22 is the same.

The horizontal axis of FIG. 9 illustrates the position (the left side in the drawing is the barrier wall 6) of the impeller 10, and the vertical axis illustrates the acting force relative to the impeller 10. When the acting force on the impeller 10 works on the barrier wall 6 side, that acting force is negative. The attractive force F1 between the permanent magnets 15, 16, the attractive force F2 between the permanent magnet 17 and the magnetic body 18, the hydrodynamic force F3 of the hydrodynamic groove 21, the hydrodynamic force F4 of the hydrodynamic groove 21, and the "net force F5 acting on the impeller," which is the total force of those, is illustrated as the acting force relative to the impeller 10.

As can be seen from FIG. 9, the emerging position of the impeller 10 is largely out of alignment from the middle position of the range of movement of the impeller 10 at the position where the net force F5 acting on the impeller 10 is zero. As a result, the distance between the impeller 10 during rotation and the barrier wall 6 narrows, and the impeller 10 touches the barrier wall 6 even when a small interference force acts relative to the impeller 10.

Figure 10:
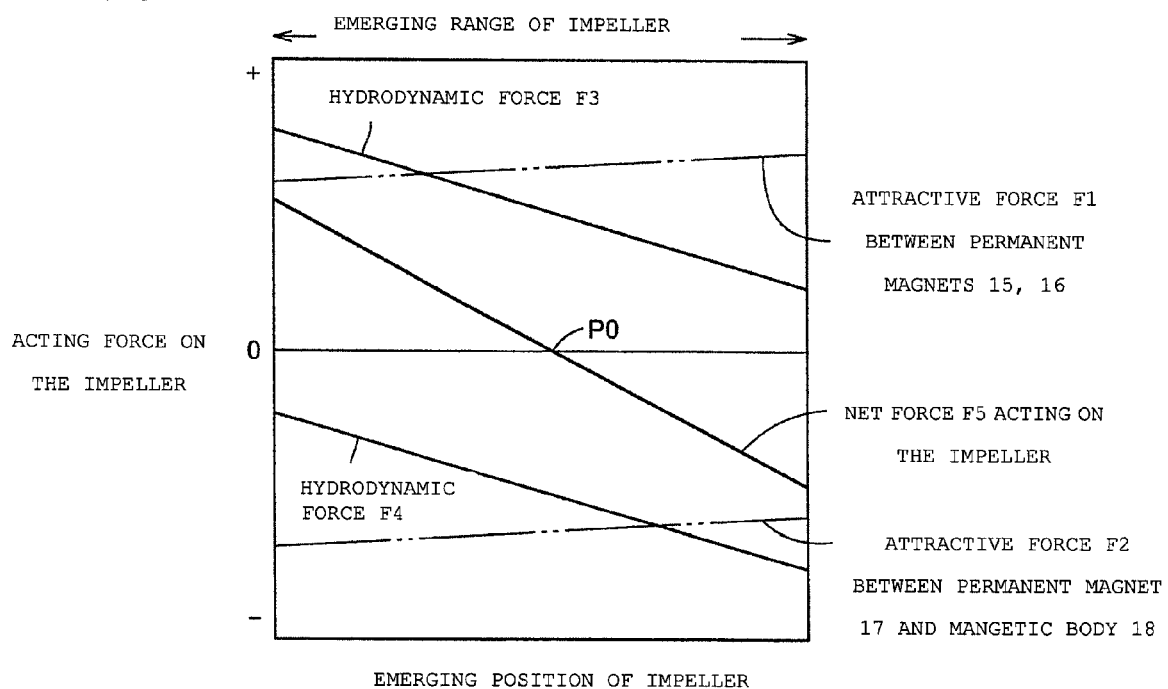
FIG. 10 is another drawing for describing an effect of the present invention.

In contrast to this, FIG. 10 is a drawing illustrating the force acting on the impeller 10 when the magnitude of the total force of an attractive force F1 between the permanent magnets 15, 16 and an attractive force F2 between the permanent magnet 17 and the magnetic body 18 is adjusted to be zero at a middle position P0 of the range of movement within the blood chamber 7 of the impeller 10. In this case, the rotational speed of the impeller 10 is maintained at the rated value as well.

Namely, the attractive force F1 between the permanent magnets 15, 16 and the attractive force F2 between the permanent magnet 17 and the magnetic body 18 are set to be the same. Additionally, the shape of the hydrodynamic grooves 21, 22 is made the same. In this case, the support rigidity relative to the emerging position of the impeller 10 is higher in comparison to that in FIG. 9. Additionally, the impeller 10 emerges at the middle position when the interference force does not act relative to the impeller 10 because the net force F5 acting on the impeller 10 is zero at the middle of the range of movement.

In this manner, the emerging position of the impeller 10 is determined by balancing out the attractive force F1 between the permanent magnets 15, 16, the attractive force F2 between the permanent magnet 17 and the magnetic body 18, and the hydrodynamic forces F3, F4 that are generated in the hydrodynamic grooves 21, 22 at the time of rotation of the impeller 10. The impeller 10 may be emerged at the same middle portion of the blood chamber 7 at the time of rotation of the impeller 10 by making F1 and F2 the same, and making hydrodynamic grooves 21, 22 the same shape. The two surfaces opposing the inner wall of the housing 2 can have the same shape and the same dimensions because the impeller 10 has a shape wherein an impeller blade is formed between two disks, as illustrated in FIG. 3 and FIG. 4. Therefore, the hydrodynamic grooves 21, 22 that have the same hydrodynamic capabilities may be provided on both sides of the impeller 10.

In this case, the impeller 10 is held in a position farthest away from the inner wall of the housing 2 because the impeller 10 is emerged in the middle position of the blood chamber 7. As a result, even if the interference force is applied to the impeller 10 while the impeller 10 is emerging, and the emerging position of the impeller 10 changes, the possibility of the impeller 10 and the inner wall of the housing 2 contacting is small, and the possibility of blood clotting and hemolysis occurring by those contacting is lowered.

Note that, in the examples in FIG. 9 and FIG. 10, the shape of the two hydrodynamic grooves 21, 22 is the same, but the shape of the hydrodynamic grooves 21, 22 may be different and the hydrodynamic capabilities of the hydrodynamic grooves 21, 22 may also be different. For example, when interference is acting consistently in one direction relative to the impeller 10 by a fluid force and the like when pumping, the impeller 10 may emerge rotating at the middle position of the housing 2 by making the capability of the hydrodynamic groove in the direction of that interference higher than the capability of the hydrodynamic groove in the other direction. As a result, the contact probability of the impeller 10 and the housing 2 can be kept low, and stabilized emerging capabilities of the impeller 10 can be obtained.

Further, satisfying the function $Kg > Ka + Kr$ is preferred, with the absolute value of the negative support rigidity value in the axial direction of the impeller 10 configured by the attractive force F1 between the permanent magnets 15, 16, and the attractive force F2 between the permanent magnet 17 and the magnetic body 18 as Ka, the absolute value of the positive rigidity value in the radial direction as Kr, and the absolute value of the positive rigidity value obtained in the two hydrodynamic grooves 21, 22 in the normal rotational speed range that rotates the impeller 10 as Kg.

Specifically, when the absolute value Ka of the negative rigidity value in the axial direction is 20,000 N/m, and the absolute value Kr of the positive rigidity value in the radial direction is 10,000 N/m, the absolute value Kg of the positive rigidity value obtained by the two hydrodynamic grooves 21, 22 in the rotational speed range that ordinarily rotates the impeller 10 is set at a value exceeding 30,000 N/m.

The support rigidity in the axial direction can be increased more than the support rigidity in the radial direction of the impeller 10 by having the function of $Kg > Ka + Kr$ because the axial support rigidity of the impeller 10 is the value of the negative rigidity based on the attractive force and the like between magnetic bodies subtracted from the rigidity attributed to the hydrodynamic force generated in the hydrodynamic grooves 21, 22. By this type of installment, when the interference force acts relative to the impeller 10, movement in the axial direction can be controlled more than movement in the radial direction of the impeller 10, and mechanical contact of the impeller 10 and the housing 2 in the forming portion of the hydrodynamic groove 21 can be avoided.

In particular, the hydrodynamic grooves 21, 22 is set recessed on a plane, as illustrated in FIG. 3 and FIG. 5; therefore, when there is mechanical contact of the housing 2 and the impeller 10 in this portion during rotation of the impeller 10, damage (roughness of the surface) occurs on the surface of either one, or both of the impeller 10 and the inner wall of the housing 2; and it can become the cause of blood clotting or hemolysis occurring if blood passes this region. The effect of raising the rigidity in the axial direction more than the rigidity in the radial direction is higher in order to prevent mechanical contact in these hydrodynamic grooves 21, 22 and control blood clotting and hemolysis.

Additionally, whirling occurs in the impeller 10 at the time of rotation if the impeller 10 is unbalanced, but this whirling is at its peak when the natural vibration frequency determined by the mass of the impeller 10 and the support rigidity value of the impeller 10, and the rotational speed of the impeller 10 are unified.

In this pump portion 1, setting the maximum rotational speed of the impeller 10 lower than the natural vibration frequency in the axial direction is preferred because the support rigidity in the radial direction is smaller than the support rigidity in the axial direction of the impeller 10. With that, in order to prevent mechanical contact of the impeller 10 and the housing 2, satisfying the function $\omega<(Kr/m)^{0.5}$ is preferred, when the radial rigidity value of the impeller 10 configured by the attractive force F1 between the permanent magnets 15, 16 and the attractive force F2 between the permanent magnet 17 and the magnetic body 18 is Kr (N/m), the mass of the impeller 10 is m (k9), and the rotational speed of the impeller is $\omega$ (rad/s).

Specifically, when the mass of the impeller 10 is 0.03 kg, and the radial rigidity value is 2000 N/m, the maximum rotational speed of the impeller 10 is set at not more than 258 rad/s (2465 rpm). Conversely, when the maximum rotational speed of the impeller 10 is set at 366 rad/s (3500 rpm), the radial rigidity is set at not less than 4018 N/m.

Furthermore, setting the maximum rotational speed of the impeller 10 to 80% or below this w is preferred. Specifically, when the mass of the impeller 10 is 0.03 kg, and the radial rigidity value is 2000 N/m, that maximum rotational speed is set at not more than 206.4 rad/s (1971 rpm). Conversely, when it is preferred that the maximum rotational speed of the impeller 10 is set at 366 rad/s (3500 rpm), the radial rigidity value is set at not less than 6279 N/m. In this manner, contacting of the impeller 10 and the housing 2 during rotation of the impeller 10 can be kept down by setting the maximum rotational speed of the impeller 10.

Additionally, when the rigidity from the hydrodynamic force of the hydrodynamic grooves 21, 22 is larger than the negative rigidity value in the axial direction of the impeller 10 configured by the attractive force F1 between the permanent magnets 15, 16 and an attractive force F2 between the permanent magnet 17 and the magnetic body 18, the impeller 10 and the housing 2 are in a non-contact state. Therefore, it is preferred that this negative rigidity value is made to be as small as possible. With that, differentiating the sizes of the opposing surfaces of the permanent magnets 15, 16 is preferred in order to kept this negative rigidity value small. For example, the change percentage of the attractive force changed by the distance between both, namely the negative rigidity, can be kept small, and a lessening of the impeller support rigidity can be prevented by making the size of the permanent magnet 16 smaller than the permanent magnet 15.

Furthermore, confirming that the impeller 10 is contacting the barrier wall 6 prior to starting the rotation of the impeller, and then starting the rotation of the impeller 10 is preferred.

Namely, when the impeller 10 is not rotating, there is no non-contact support from the hydrodynamic grooves 21, 22, and furthermore, the impeller 10 and the housing 2 are in contact with high compression by the attractive force F1 between the permanent magnets 15, 16 and the attractive force F2 between the permanent magnet 17 and the magnetic body 18. Additionally, like this pump portion 1, when the impeller 10 is rotated with magnetic interaction of the coil 20 and the magnetic body 18 within the motor chamber 8 and the permanent magnet 17 of the impeller 10, the starting torque is small compared to when the impeller illustrated in FIG. 3 of Patent Document 2 is rotatably driven with magnetic coupling between permanent magnets. Therefore, initiating rotation of the impeller 10 smoothly is difficult.

However, when the shroud 12 of the impeller 10 is in contact with the barrier wall 6, the permanent magnet 17 of the impeller 10 and the magnetic body 18 of the motor chamber 8 are close compared to when the shroud 11 of the impeller 10 is in contact with the inner wall of the blood chamber 7, therefore, the rotary torque when starting the impeller 10 can be made higher and the impeller 10 can start rotation smoothly.

Nevertheless, according to that described above, at the time of rotation of the impeller 10, the attractive force F1 between the permanent magnets 15, 16, and the attractive force F2 between the permanent magnet 17 and the magnetic body 18 are not restricted to when the impeller 10 stops, and the impeller 10 is not necessarily in contact with the barrier wall 6 because the position of the impeller 10 is set to balance out in the vicinity of the middle of the range of movement of the impeller 10.

With that, in this centrifugal blood pump device, means to transfer the impeller 10 to the barrier wall 6 side prior to starting rotation of the impeller 10 is provided. Specifically, an electrical current is passed through the plurality of coils 20, and the impeller 10 is moved to the barrier wall 6 side so that the attractive force F2 between the permanent magnet 17 and the magnetic body 18 becomes larger.

Figure 11:
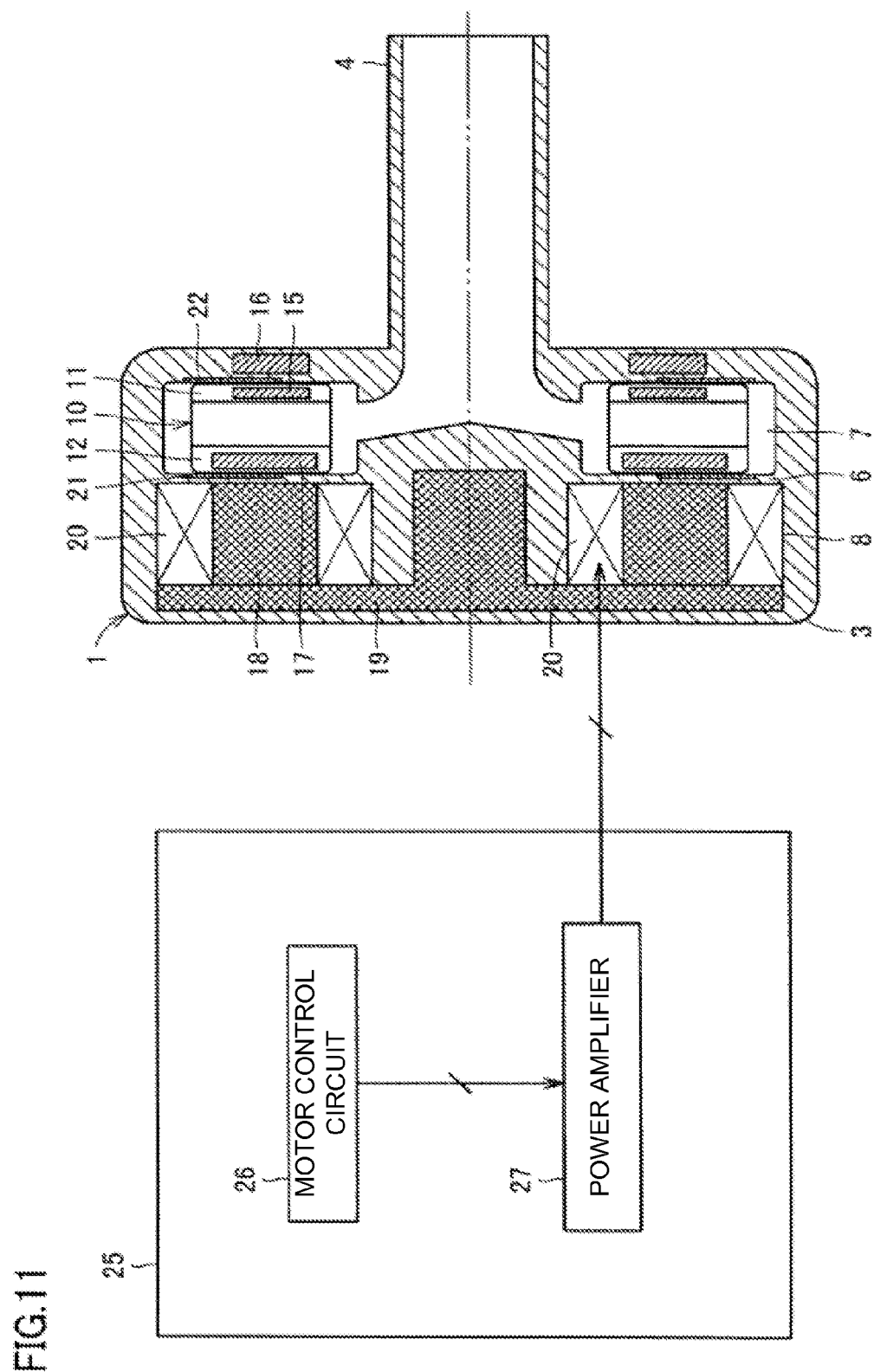
FIG. 11 is a block diagram illustrating the configuration of the controller controlling the pump portion illustrated in FIG. 1 to FIG. 7.

FIG. 11 is a block diagram illustrating a configuration of a controller 25 that controls the pump portion 1. In FIG. 11, the controller 25 includes a motor control circuit 26 and a power amplifier 27. The motor control circuit 26 outputs a control signal of, for example, three phases of a 120 degree excitation method. The power amplifier 27 amplifies the three phase control signal from the motor control circuit 26 and generates three phase voltages VU, VV, VW illustrated in FIG. 8. The three phase voltages VU, VV, VW are applied to the first through third coils, respectively, described in FIG. 7 and FIG. 8. During normal operation, as a result of this, the impeller 10 rotates at a predetermined rotational speed in a center position in a movement range.

Figure 12:
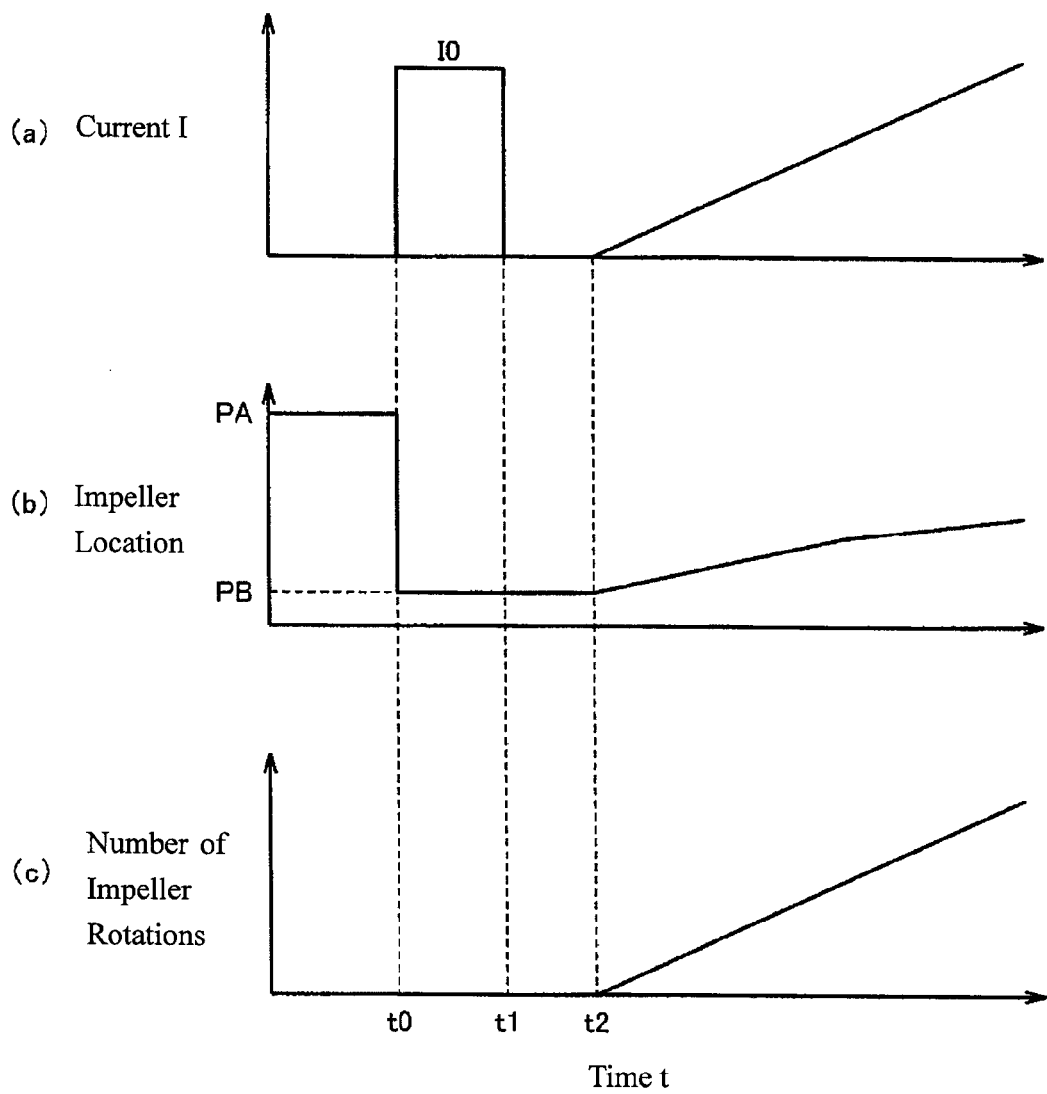
FIG. 12 is a time chart illustrating the actions of the controller illustrated in FIG. 11.

FIGS. 12 (a) to (c) are time charts illustrating a coil current I when the rotation of the impeller 10 starts, the position of the impeller 10, and the time change in the rotational speed of the impeller 10. In FIGS. 12 (a) to (c) in the initial state, the shroud 11 of the impeller 10 is in contact with the inside wall of the blood chamber 7 due to the attractive force of the permanent magnets 15, 16, and the impeller 10 is in a position PA. Because it is difficult for the impeller 10 to rotate in that state, the shroud 12 of the impeller 10 moves the impeller 10 to a position PB in contact with the barrier wall 6.

In the time t0, a voltage of any pattern from the voltages VU, VV, VW of the 6 patterns (0 to 60 degrees, 60 to 120 degrees, . . . , 300 to 360 degrees) illustrated in FIG. 8 is applied to the first to third coils 20, and the predetermined current I0 flows to the coils 20. When the current I0 flows to the coils 20, the attractive force F2 between the permanent magnet 17 and the magnetic body 18 grows larger than the attractive force F1 between the permanent magnets 15, 16, the impeller 10 moves to the position PB on the barrier wall 6 side without substantially turning, and the shroud 12 of the impeller 10 contacts the barrier wall 6. After the impeller 10 moves to the position PB the current I0 is cut off (time t1).

Note that, moving the impeller 10 without rotation is because the movement of the impeller 10 is impeded by the hydrodynamic bearing effect of the hydrodynamic groove 21 even if the impeller 10 is moved to the position PB on the barrier wall 6 side while rotating. Furthermore, a sensor that detects the position in the blood chamber 7 of the impeller 10 is provided, and after it is confirmed that the impeller 10 has contacted the barrier wall 6, it is preferred to cut off the current I0.

Next, the three phase voltages VU, VV, VW are applied to the first to third coils 20 described in FIG. 8, and the coil current I is gradually raised to the predetermined rated values. At this time, the impeller 10 rotates smoothly because the impeller 10 is in contact with the barrier wall 6. In conjunction with the raising of the coil current I, the impeller 10 moves to a center position of the movement range from the position PB of the barrier wall 6.

Note that, upon startup when the voltages VU, VV, VW of the 6 patterns (0 to 60 degrees, 60 to 120 degrees, . . . , 300 to 360 degrees) are applied to the first to third coils 20, the pattern when the attractive force between the permanent magnet 17 and the magnetic body 18 is at its largest is different depending on the positional relationship of the permanent magnet 17 and the magnetic body 18. Therefore, during startup, rather than applying only the voltages VU, VV, VW of a fixed pattern to the first to third coils 20, the voltages VU, VV, VW of the 6 patterns may be sequentially applied in fixed intervals to the first to the third coils 20. In this situation, the impeller 10 slightly rotates (strictly not more than ¼ turn, that is, not more than 360 degrees electrical angle rotation) and moves to the position PB on the barrier wall 6 side.

Furthermore, when the voltage VU, VV, VW of the 6 patterns is applied, six magnetic bodies among the nine magnetic bodies 18 become N poles or S poles without current flowing in any coil 20 among the first to third coils 20, and the remaining three magnetic bodies 18 do not generate magnetic poles. Therefore, the current flows to all of the first to third coils 20, each of the nine magnetic bodies 18 applies voltage to the first to third coils 20 so as to become N-poles or S-poles, and the attractive force between the permanent magnet 17 and the magnetic body 18 may be strengthened.

Figure 13:
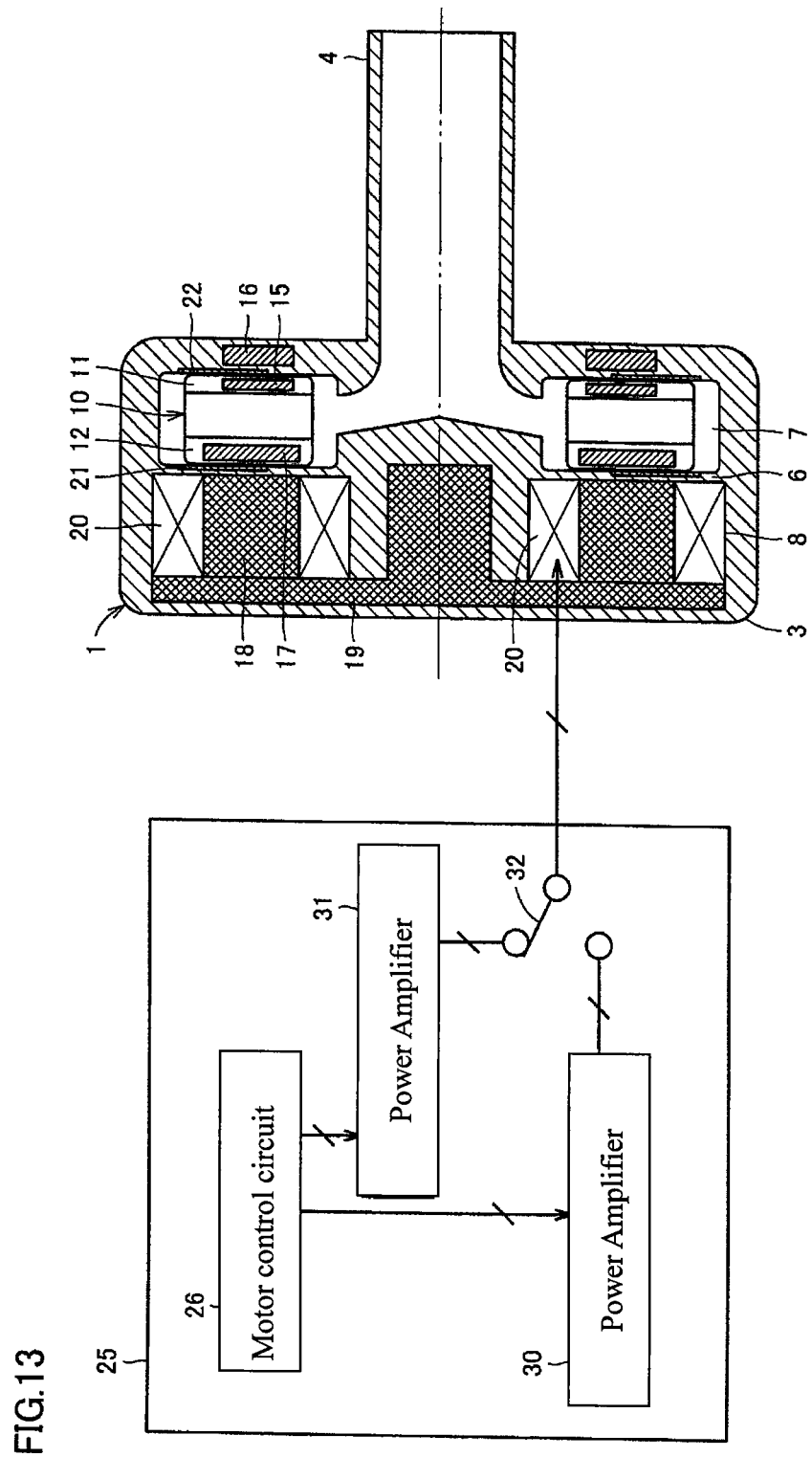
FIG. 13 is a block diagram illustrating an alternative example of the first embodiment.

Furthermore, FIG. 13 is a block diagram illustrating an alternative example of the first embodiment. In this alternative example, the power during and after the rotation startup of the impeller 10 is switched. That is, in FIG. 13, in this alternative example, the power amplifier 27 in FIG. 11 is replaced by the power amplifiers 30, 31 and the change-over switch 32. In the time t0 to t1 in FIG. 12, the output signal of motor control circuit 26 is given to the power amplifier 30, the output voltage of the power amplifier 30 is applied to the coil 20 via the change-over switch 32, and the current I0 flows to the coil 20. After time t2, the output signal of motor control circuit 26 is given to the power amplifier 31, the output voltage of the power amplifier 31 is applied to the coil 20 via the change-over switch 32, and current flows to the coil 20.

Figure 14:
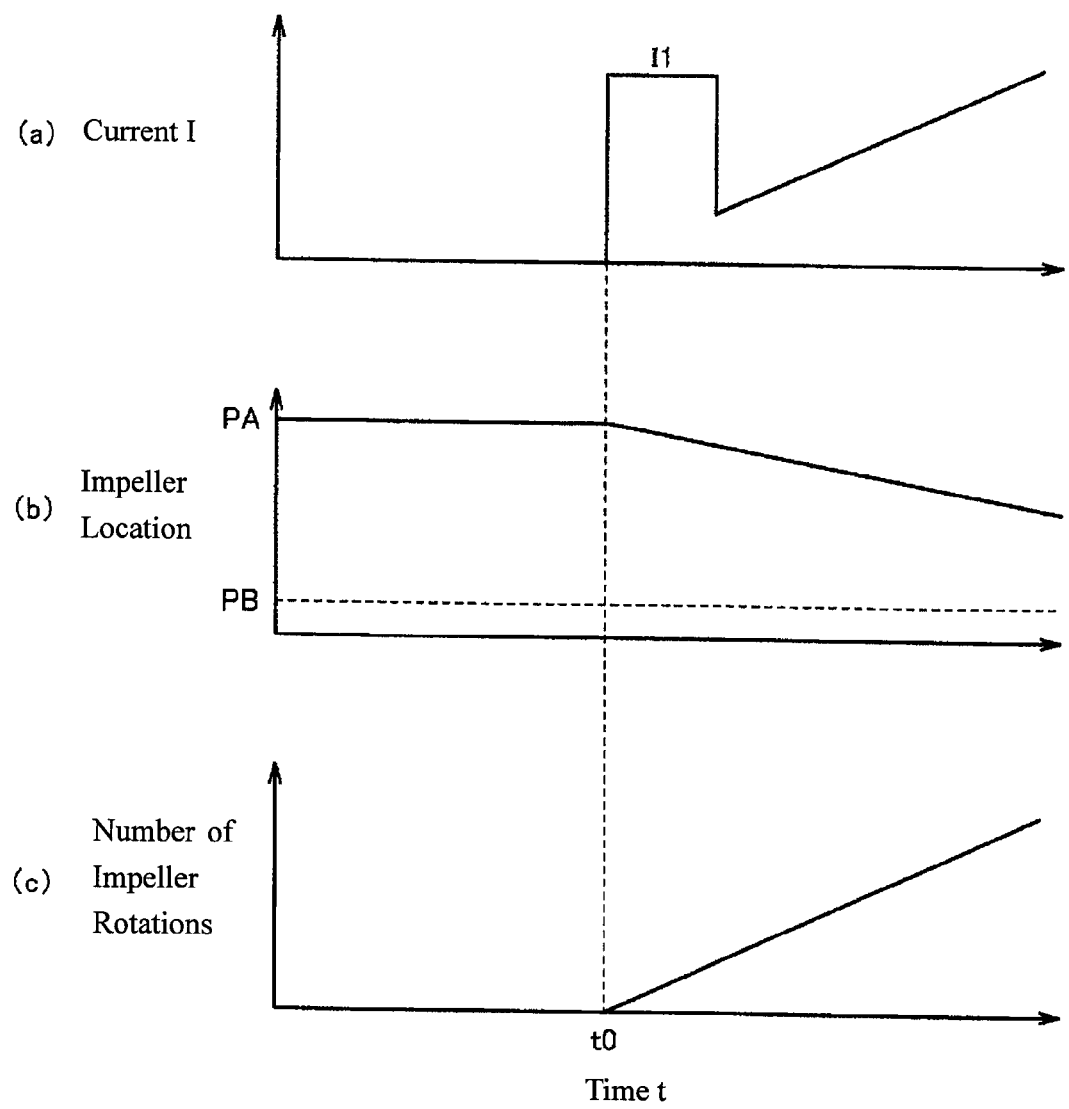
FIG. 14 is a time chart illustrating another alternative example of the first embodiment.

Furthermore, FIGS. 14 (a) to (c) are time charts that illustrate another alternative example of the first embodiment. In FIGS. 14 (a) to (c) in the initial state, the shroud 11 of the impeller 10 is in contact with the inside wall of the blood chamber 7, and the impeller 10 is in the position PA. In the time t0, the predetermined current I1 is caused to flow to the coil 20. That is, for example, the three phase control signal of the 120 degree excitation method is generated by the motor control circuit 26. The power amplifier 27 amplifies the control signal of the three phases from the motor control circuit 26 and generates the three phase voltages VU, VV, VW illustrated in FIG. 8. The three phase voltages VU, VV, VW are applied to the first through third coils 20, respectively, described in FIG. 7 and FIG. 8.

Therefore, a rotating magnetic field is applied to the impeller 10 by the current I1. This current I1 is a current larger than the current I0 in FIG. 12, and it is a current that can start the rotation of the impeller 10 even when the shroud 11 of the impeller 10 is in contact with the inside wall of the blood chamber 7. After the rotation startup is confirmed, the coil current I is lowered and gradually raised to a predetermined rated value. Even when the impeller 10 is on the position PA side in this manner, it may be configured so an excessive current flows to the coils 20 only when the impeller 10 starts up rotation.

Furthermore, a DLC (diamond-like carbon) film may be formed on at least one of the surface of the inside wall and the surface of the barrier wall 6 of the blood chamber 7 and the surface of the impeller 10. As a result, the frictional force between the impeller 10 and the inside wall of the blood chamber 7 and the barrier wall 6 is reduced, and the impeller 10 can start up rotation smoothly. Note that, a fluorine-based resin film, a paraxylene resin film or the like may be used instead of the diamond-like carbon film.

Figure 15:
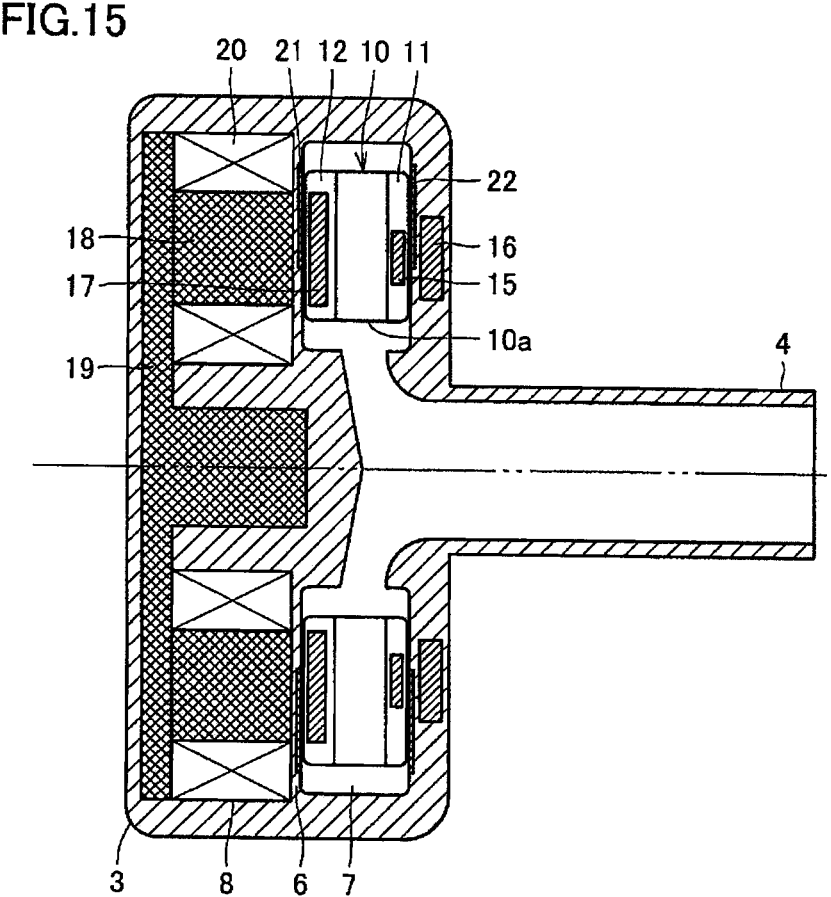
FIG. 15 is a cross sectional view illustrating yet another alternative example of the first embodiment.

Furthermore, FIG. 15 is a cross sectional view illustrating another alternative example of the first embodiment and is a diagram comparable to FIG. 3. In FIG. 15, in this alternative example, the sizes of the opposing surfaces of the opposing permanent magnets 15, 16 are different. FIG. 3 illustrates when the sizes of the opposing surfaces of the permanent magnets 15, 16 are the same, however, by having the sizes of the opposing surfaces of the permanent magnets 15, 16 to be different, the amount of change of the attractive force that changes from the distance between the two, that is, the negative rigidity, can be suppressed to be small and a lowering of the support rigidity of the impeller 10 can be prevented.

Figure 16:
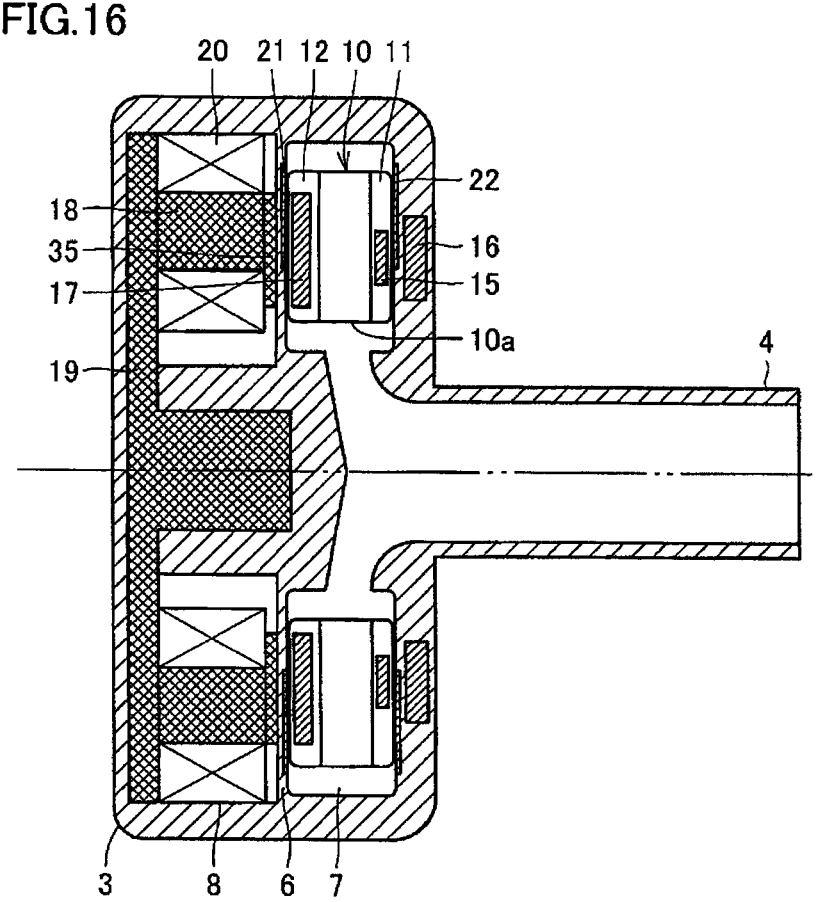
FIG. 16 is a cross sectional view illustrating yet another alternative example of the first embodiment.
Figure 17:
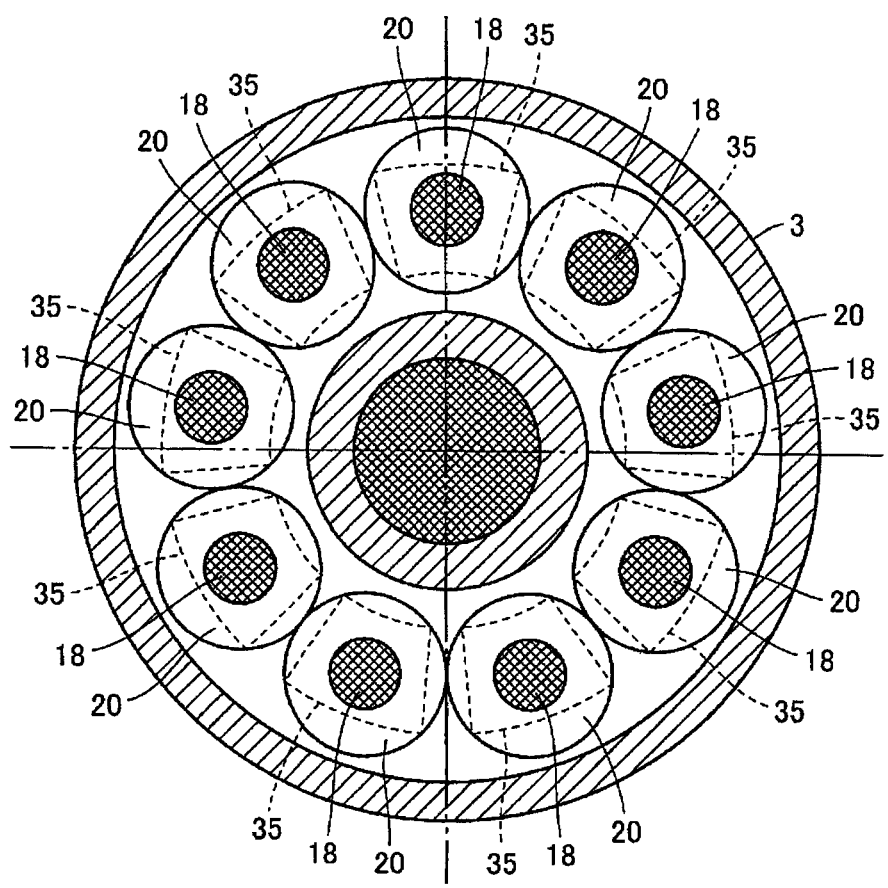
FIG. 17 is a cross sectional view exemplifying the shape of the magnetic body 35 illustrated in FIG. 16.

Furthermore, FIG. 16 is a cross sectional view illustrating another alternative example of the first embodiment and is a diagram comparable to FIG. 15. In FIG. 16, in the alternative example, a magnetic body 35 is provided on the end surface opposite the permanent magnet 17 of each magnetic body 18. The area of the surface opposing the permanent magnet 17 of the magnetic body 35 is larger than the area of the end surface of the magnetic body 18. Furthermore, it is desirable that the surface opposing the permanent magnet 17 of the magnetic body 35 is triangular or fan shaped. Furthermore, as illustrated in FIG. 17, it is desirable that the sides opposing each other of the two adjacent magnetic bodies 35 are provided substantially parallel.

As illustrated in FIG. 7, in a typical axial gap type motor, the magnetic body 18 is often triangular prism shaped or fan shaped, furthermore, the end surfaces of the magnetic body 18 are often directly opposite the permanent magnet 17 without being provided with the magnetic body 35. This is because a magnetic flux for generating torque can be given uniformly to the change-over line of the magnetic poles of the permanent magnet 17 (border of the N-pole and S-pole) and the energy efficiency in the rotary drive of the impeller 10 can be increased when a triangular prism shaped or fan shaped magnetic body 18 is used. Furthermore, having the end surfaces of the magnetic body 18 directly opposite the permanent magnet 17 without providing the magnetic body 35 allows for simplification of the motor configuration and lessening the number of components.

However, in order to reduce copper loss in the coil 20 and increase the motor efficiency as described in FIG. 7 of the first embodiment, a cylindrical shaped magnetic body 18 is used. When the end surfaces of the cylindrical shaped magnetic body 18 are directly opposite the permanent magnet 17, the participation efficiency of the magnetic flux for generating torque becomes lower from the change-over line of the magnetic poles of the permanent magnet 17 (border of the N-pole and S-pole), and the energy efficiency in the rotary drive of the impeller 10 cannot be increased.

Furthermore, in the pump device of the first embodiment, it is necessary to precisely adjust the balance between the attractive force generated on the permanent magnet 15, 16 side and the attractive force generated on the permanent magnet 17 side. At that time, in the configuration with the end surfaces of the cylindrical magnetic body 18 directly opposite the permanent magnet 17, this setting (adjustment) of the attractive force value becomes difficult. That is, the attractive force value depends on the size of the ratio of the opposing areas of the magnetic body 18 and the permanent magnet 17. In order to adjust the attractive force value, when the cross sectional area of the magnetic body 18 is changed, it is necessary to re-wind the coil 20 and reassemble the motor body every time it is changed, and labor increases.

Meanwhile, when the triangular or fan shaped magnetic body 35 is separately provided on the ends of the magnetic body 18, the energy efficiency in the rotary drive of the impeller 10 is increased, further, by only adjusting the area of the magnetic body 35, the balance of the attractive force generated on the permanent magnet 15, 16 side can be easily set (adjusted).

Figure 18:
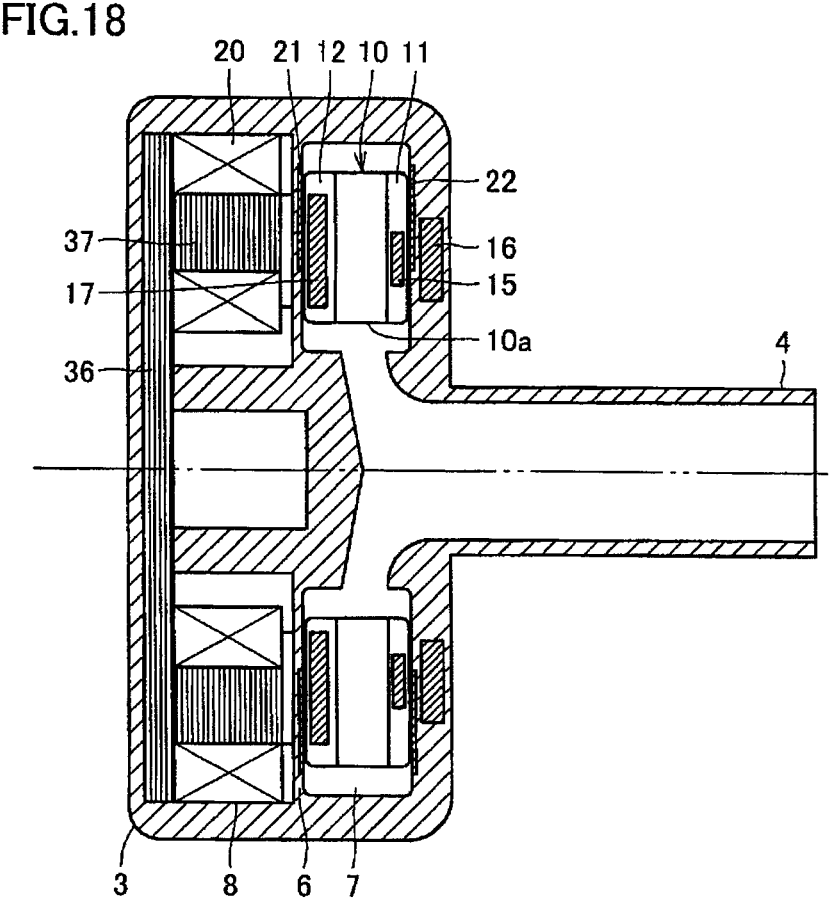
FIG. 18 is a cross sectional view illustrating yet another alternative example of the first embodiment.

Furthermore, FIG. 18 is a cross sectional view illustrating another alternative example of the first embodiment and is a diagram comparable to FIG. 15. In FIG. 18, in this alternative example, the yoke 19 is replaced by a yoke 36, and the magnetic body 18 is replaced by a magnetic body 37. The yoke 36 and the magnetic body 37, respectively, include a plurality of steel plates stacked in the length direction of the rotational axis of the impeller 10. In this alternative example, eddy current loss generated by the yoke 36 and the magnetic body 37 can be reduced, and energy efficiency in the rotary drive of the impeller 10 can be increased.

Figure 19:
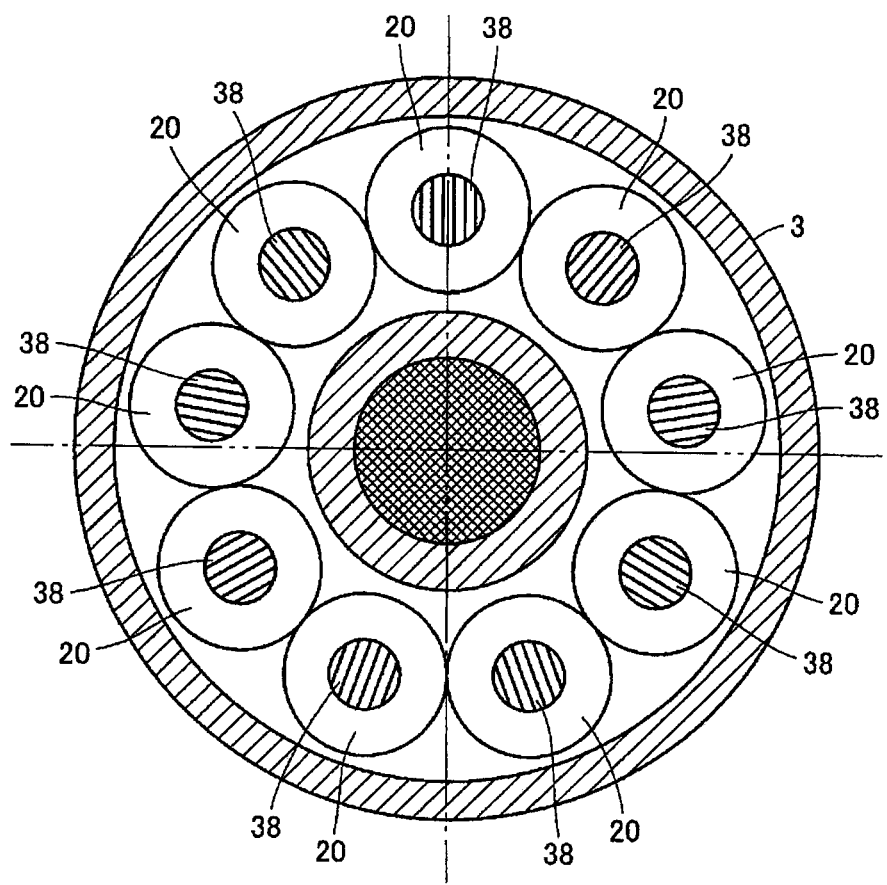
FIG. 19 is a cross sectional view illustrating yet another alternative example of the first embodiment.
Figure 20:
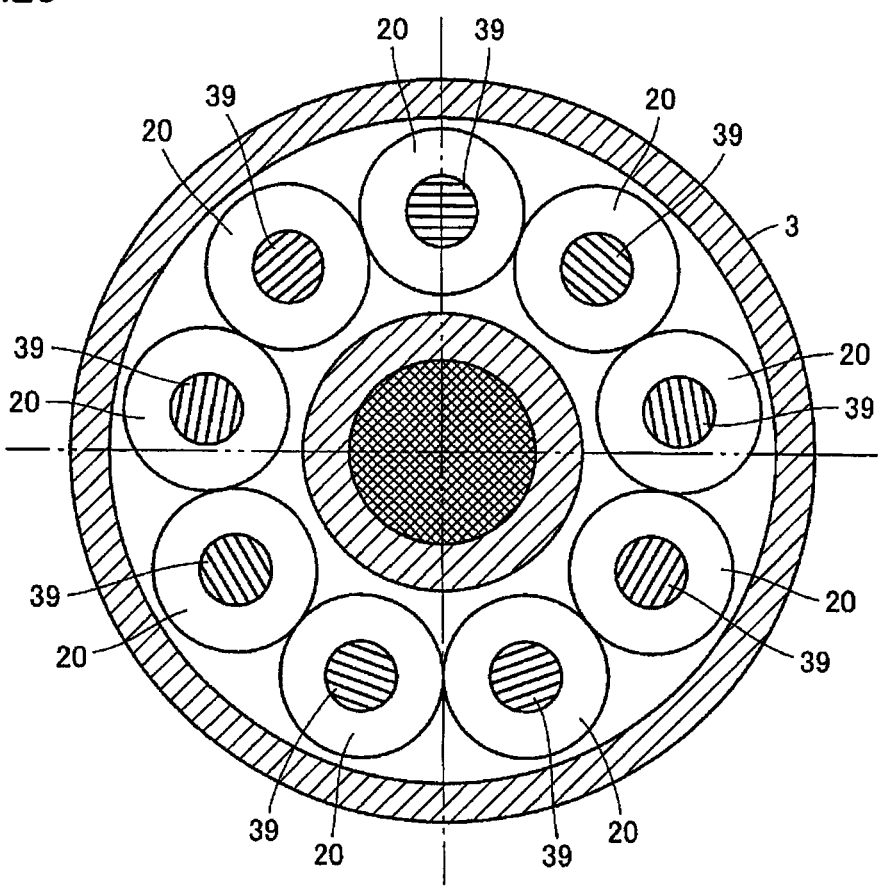
FIG. 20 is a cross sectional view illustrating yet another alternative example of the first embodiment.

Furthermore, as illustrated in FIG. 19, the magnetic body 37 can be replace by a magnetic body 38 that includes a plurality of steel plates stacked in the rotation direction of the impeller 10. Furthermore, as illustrated in FIG. 20, the magnetic body 37 can be replaced by a magnetic body 39 that includes a plurality of steel plates stacked in the radial direction of the impeller 10. The same effect as in the alternative example of FIG. 18 can be achieved in this situation as well.

Furthermore, the yoke 19 and magnetic body 18 of FIG. 3, respectively, may be formed of pure iron, soft iron, or ferro-silicon. In this case, iron loss of the yoke 19 and the magnetic body 18 can be reduced, and energy efficiency in the rotary drive of the impeller 10 can be increased.

Figure 21:
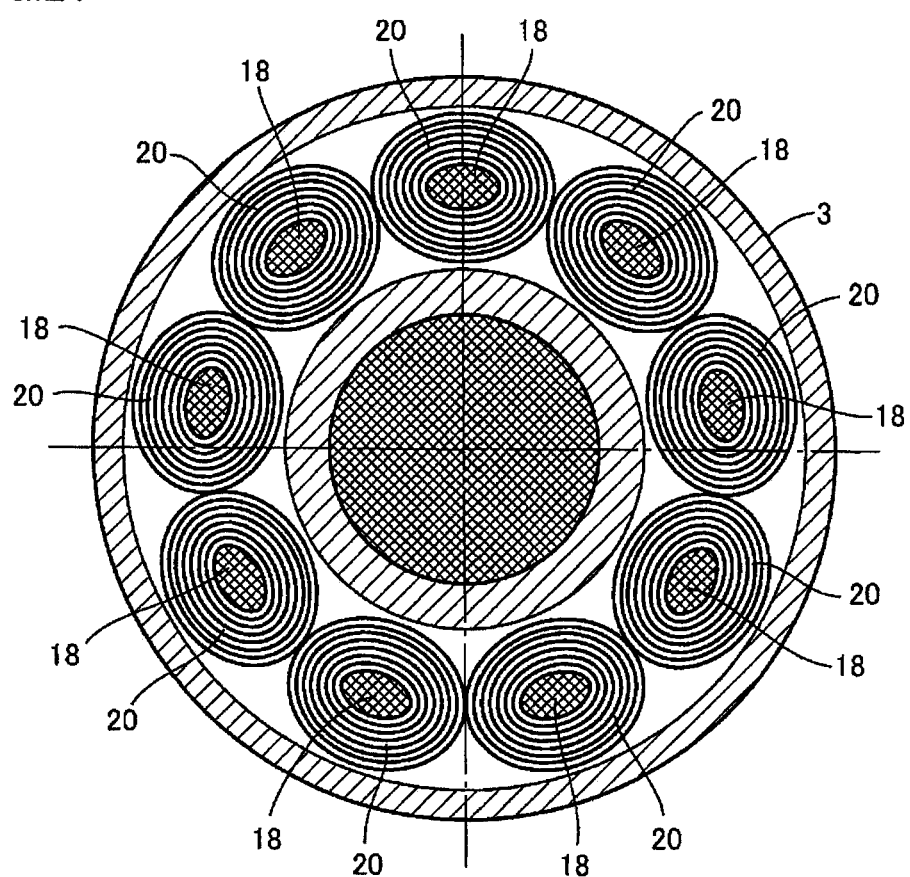
FIG. 21 is a cross sectional view illustrating yet another alternative example of the first embodiment.
Figure 22:
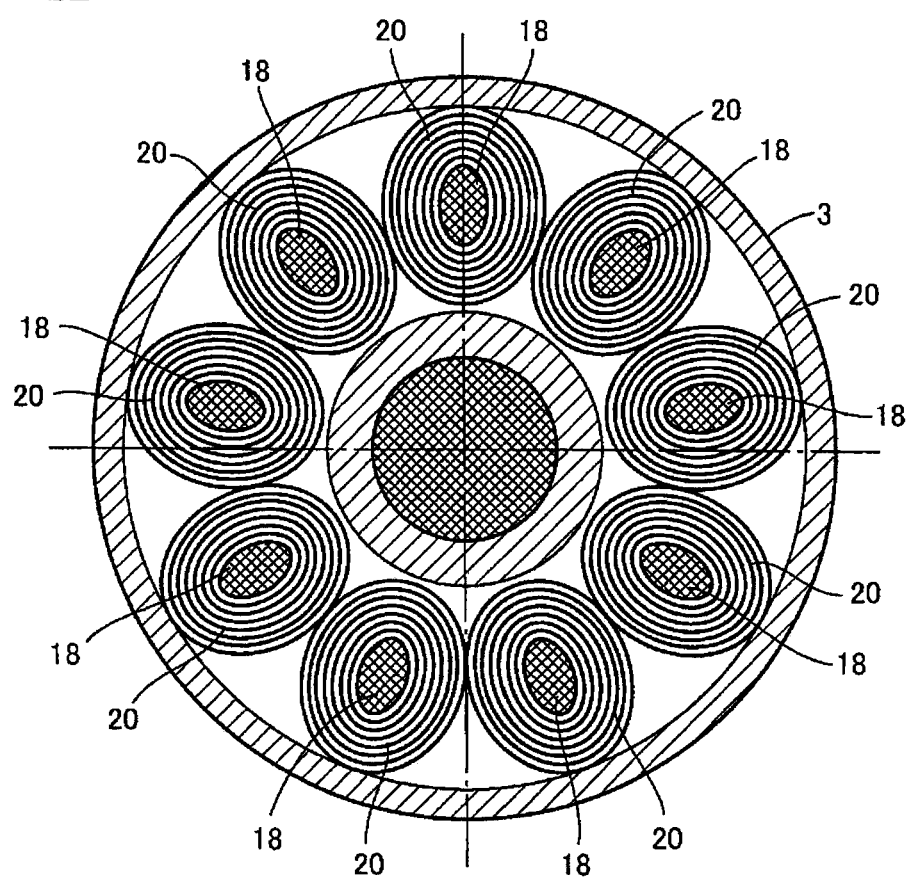
FIG. 22 is a cross sectional view illustrating yet another alternative example of the first embodiment.

Furthermore, FIG. 21 is a cross sectional view illustrating another alternative example of the first embodiment and is a diagram comparable to FIG. 7. In FIG. 21, in the alternative example, the cross sectional shape of the magnetic body 18 is elliptical when the magnetic body 18 is cut in a perpendicular plane to the axis of the magnetic body 18. That is, the cross sectional shape of the magnetic body 18 is not limited to a perfect circle, but may also be elliptical with an ellipticity of 0.5 or more. However, the ellipticity is a comparison (minor axis/major axis) of the minor axis (length of the minor axis) and the major axis (length of the major axis) of the ellipse. The ellipticity of the magnetic body 18 is decided according to the size of the inner and outer diameters of the space for the coils 20 and the number of slots in the motor. The plurality of magnetic bodies 18 is disposed at equal angular intervals along the same circle. As illustrated in FIG. 21, the major axis of the ellipse may face the tangential direction, or as illustrated in FIG. 22, the minor axis of the ellipse may face the tangential direction. Even in these alternative examples, there are no corners in the outer periphery of the magnetic body 18, therefore, the coil 20 can be easily wound, furthermore, a large space for the coils 20 can be ensured.

[Second Embodiment]

Figure 23:
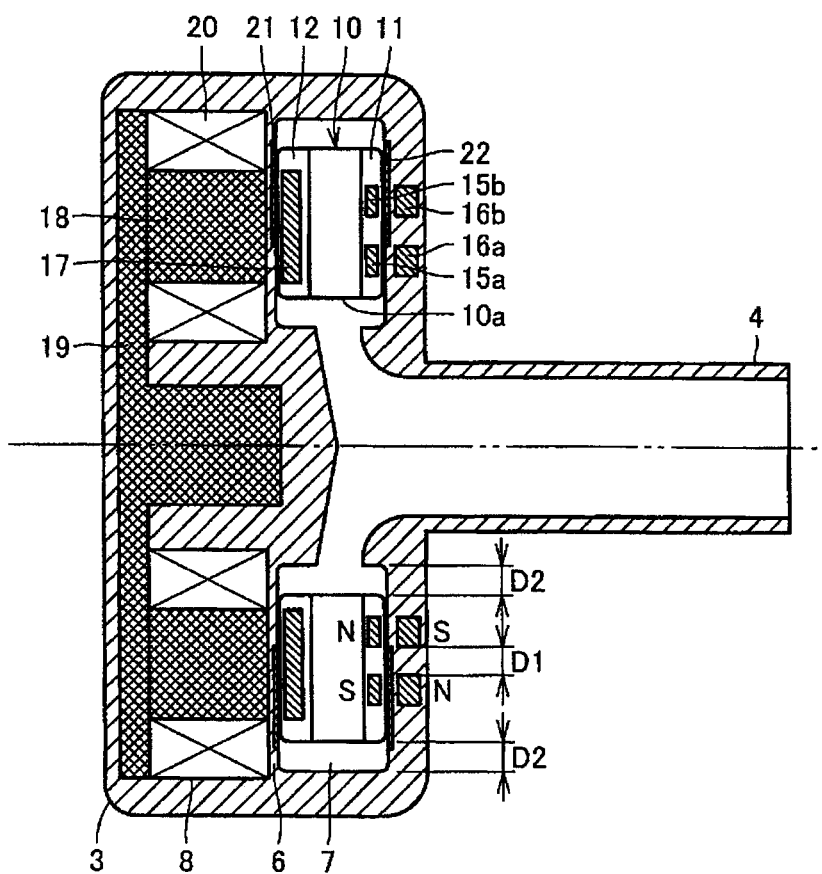
FIG. 23 is a cross sectional view illustrating the configuration of the pump portion of the centrifugal blood pump device according to the second embodiment of this invention.

FIG. 23 is a cross sectional view illustrating the configuration of a pump portion of the centrifugal blood pump device according to a second embodiment of the present invention, and is a diagram comparable to FIG. 3. In FIG. 23, permanent magnets 15a, 15b are embedded in the shroud 11, and permanent magnets 16a, 16b that attract the permanent magnets 15a, 15b, respectively, are embedded in the inner wall of the blood chamber 7 opposing that shroud 11.

The permanent magnets 15a, 15b, respectively, are formed annularly and the outer diameter of the permanent magnet 15a is smaller than the inner diameter of the permanent magnet 15b. The permanent magnets 15a, 15b are formed coaxially, and the center point of the permanent magnets 15a, 15b are disposed on the rotation center line of the impeller 10. The end surface of permanent magnets 15a, 15b in the same direction are different poles, however, the configuration may be the same poles.

Furthermore, the permanent magnets 16a, 16b, respectively, are provided annularly, and the outer diameter and inner diameter of the permanent magnet 16a are the same as the outer diameter and the inner diameter of the permanent magnet 15a. The outer diameter and inner diameter of the permanent magnet 16b are the same as the outer diameter and inner diameter of the permanent magnet 15b. The permanent magnets 16a, 16b are provided coaxially, and the center point of the permanent magnets 16a, 16b are disposed on the center line of the side wall of a cylinder of the blood chamber 7. The end surface of permanent magnets 16a, 16b in the same direction are different poles, however, the configuration may be the same poles. The permanent magnets 15a and 16a, and the permanent magnets 15b and 16b, respectively, are disposed to have two opposing poles attracting each other.

Furthermore, the spacing (that is, the spacing between the permanent magnets 16a, 16b) D1 between the permanent magnets 15a, 15b is set larger than the distance D2, which is one-half the moveable distance (that is, the difference in distance between the inner diameter of the blood chamber 7 and the outer diameter of the impeller 10) in the radial direction of the impeller 10 (D1>D2). This is because, if D1<D2, when the impeller moves to the utmost radial direction, the permanent magnets 15a and 16a, and the permanent magnets 15b and 16b, respectively, interfere, and the restoring force that restores the impeller 10 to the pump center position becomes unstable. Note that, when there is a protruding portion in the inner wall of the blood chamber 7, the moveable distance in the radial direction of the impeller 10 is the difference in distance between the inner diameter of the protruding portion in the inner wall of the blood chamber 7 and the outer diameter of the impeller 10.

In this second embodiment, the support rigidity in the radial direction of the impeller can be greater because two pairs of permanent magnets 15a, 16a and permanent magnets 15b, 16b are provided in the radial direction of the impeller 10 compared to when only one pair of permanent magnets are provided in the radial direction of the impeller 10.

Figure 24:
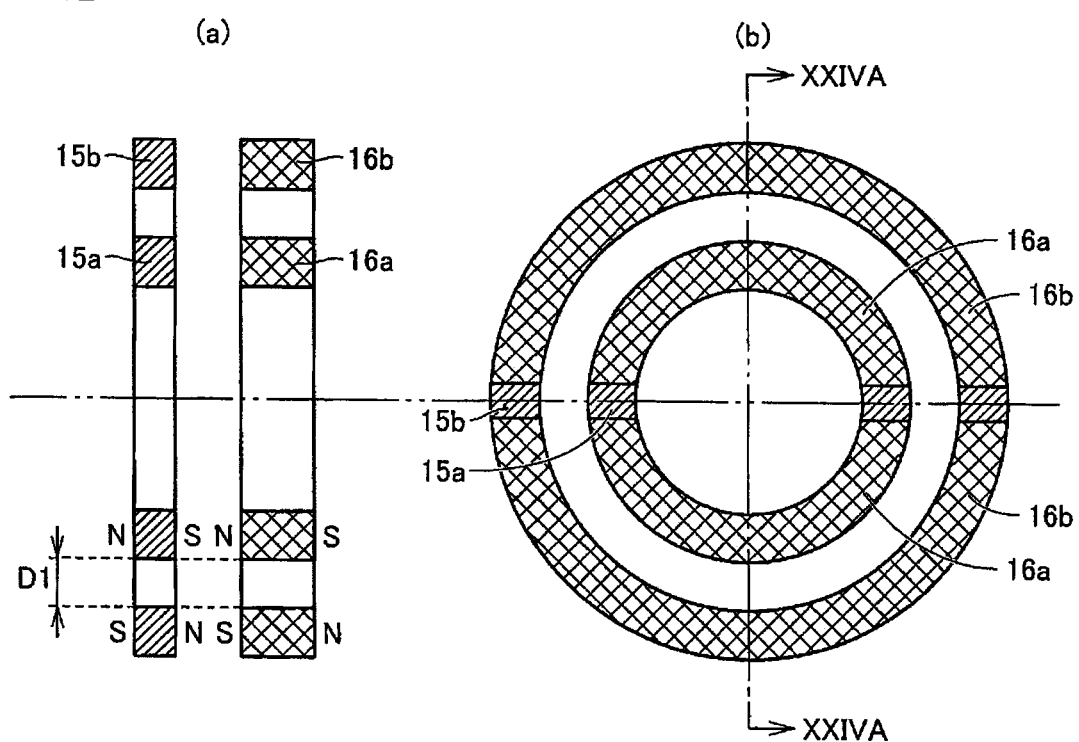
FIG. 24 is a cross sectional view illustrating the main sections of an alternative example of the second embodiment.

FIGS. 24 (a) and (b) are diagrams illustrating the main section of the alternative example of the second embodiment, and are diagrams illustrating the configuration of the permanent magnets 15a, 15b, 16a, 16b. FIG. 24 (a) is a XXIVA-XXIVA line cross sectional view of FIG. 24 (b). In this alternative example, as illustrated in FIGS. 24 (a) and (b), the permanent magnets 15a, 15b, respectively, are formed annularly and the outer diameter of the permanent magnet 15a is smaller than the inner diameter of the permanent magnet 15b. Meanwhile, the permanent magnets 16a, 16b, respectively, are formed in an arc shape and the two are arrayed in the rotation direction of the impeller 10. The outer diameter and inner diameter of the two permanent magnets 16a disposed annularly and are the same as the outer diameter and inner diameter of the permanent magnet 15a. The outer diameter and inner diameter of the two permanent magnets 16b disposed annularly and are the same as the outer diameter and inner diameter of the permanent magnet 15b. The same effect as in the second embodiment can be achieved in the alternative example as well.

[Third Embodiment]

In the centrifugal blood pump device of the first and second embodiments, by rotating the impeller 10, blood flows from a blood inflow port 4 to a blood outflow port 5 through an opening 7a, and pressure distribution of the blood is generated in the blood chamber 7. In particular, when the discharge flow rate of the blood is large, the difference between the pressure on the opening 7a side and the pressure on the opposite side of the opening 7a increases, as illustrated in FIG. 25, the impeller 10 inclines in a state with the distance between the impeller 10 and the permanent magnets 16a, 16b on the opening 7a side smaller than the distance between the impeller 10 and the permanent magnets 16a, 16b on the opposite side of the opening 7a while the impeller 10 is attracted to the opening 7a side.

Figure 25:
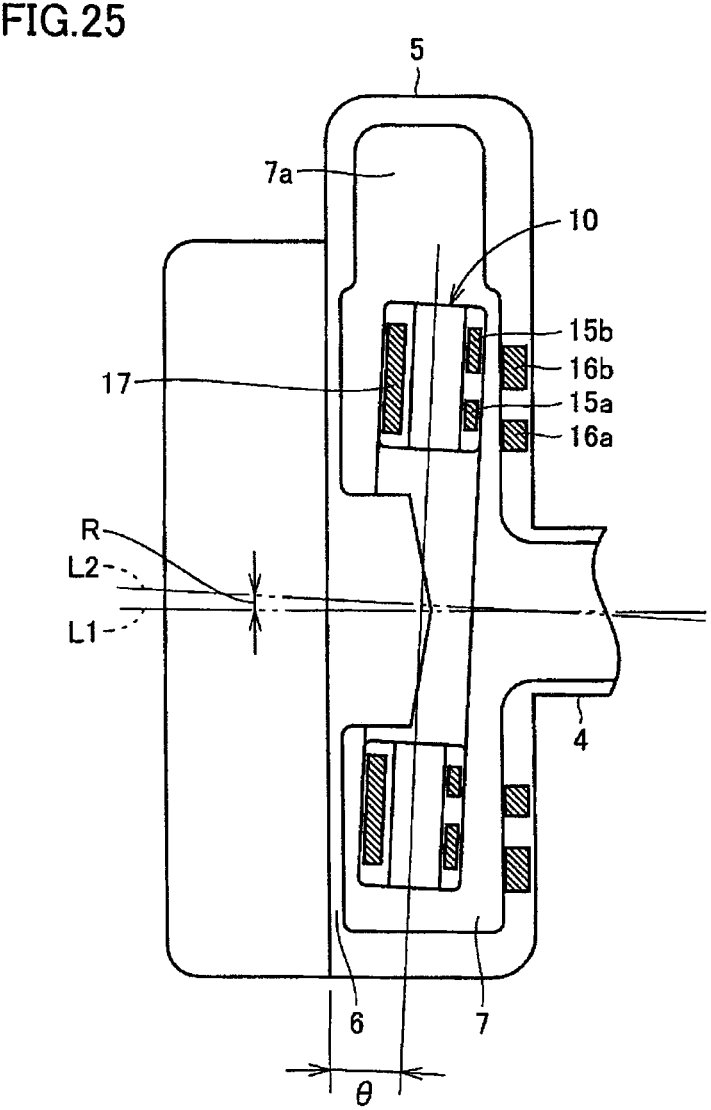
FIG. 25 is a cross sectional view for describing problems of the centrifugal blood pump device.

In FIG. 25, a state is illustrated where a rotation center line L2 of the impeller moves to the opening 7a side to a distance R rather than a center line L1 of the side wall of the cylinder of the blood chamber 7. Furthermore, a state is illustrated where a plane that includes the barrier wall 6 and a plane that includes the center surface of the impeller intersect at an angle θ without the barrier wall 6 and the impeller 10 being parallel.

Figure 26:
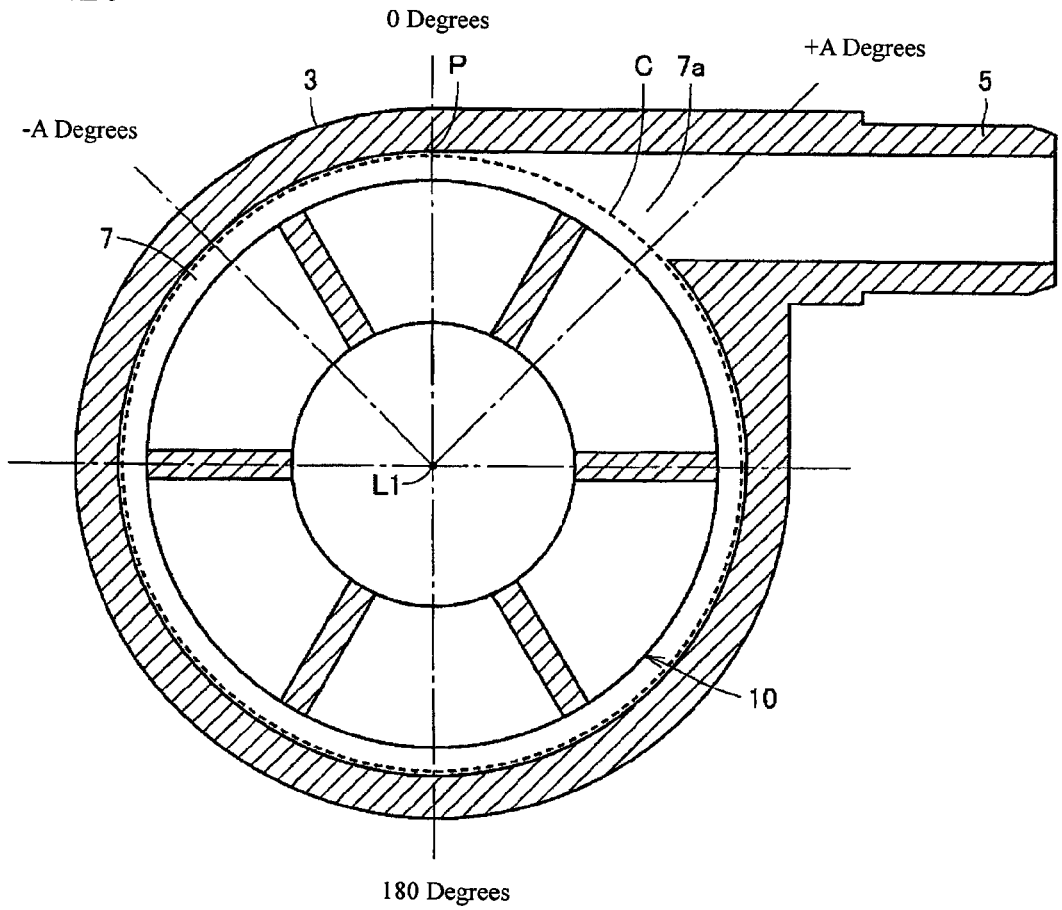
FIG. 26 is a cross sectional view for describing a method for solving the problems described in FIG. 25.

FIG. 26 is a diagram that illustrates a positional relationship between the center line L1 and the opening 7a of the side wall of the blood chamber 7. In FIG. 26, a housing 2 is orthogonal to the center line L1 of the side wall of the blood chamber 7 and is cut by the plane that includes the center line of an aperture of the blood outflow port 5. The side wall of the blood chamber 7 is formed along the circle C on the plane. The center point of circle C is an intersection of that plane and the center line L1 of the side wall of the blood chamber 7. The aperture of blood outflow port 5 extends to the tangential direction of circle C. In FIG. 26, the impeller 10 rotates in the clockwise direction, and the blood also rotates in that direction. The contact point P of the aperture of the blood outflow port 5 and circle C are located at the end of the upstream (the right side on the center of FIG. 26) of the opening 7a on the side wall of the blood chamber 7.

Herein, the direction of the contact point P (the end of the upstream side of the opening 7a) is 0 degrees as viewed from the center point (the center line L1 of the side wall of the blood chamber 7) of the circle C and the opposite direction is 180 degrees. The emerging position of the impeller 10 is decided by the balance between the fluid force of the blood, the hydrodynamic pressure of the hydrodynamic bearing, the attractive force between the permanent magnets 15a, 15b and the permanent magnets 16a, 16b, the attractive force between the permanent magnet 17 on the impeller side 10 and the magnetic body 18 on the motor side, and the like. In this third embodiment, the attractive force of the permanent magnets 15a, 15b and the permanent magnets 16a, 16b in the opening 7a side (in the range of 0 degrees±A degrees) is set smaller than the attractive force of the permanent magnets 15a, 15b and the permanent magnets 16a, 16b in the opposite side of the opening 7a in order to suppress the inclining of the impeller 10. Herein, A degrees is an angle predetermined larger than 0 degrees and less than 180 degrees. Preferably, A degrees is 60 degrees.

Figure 27:
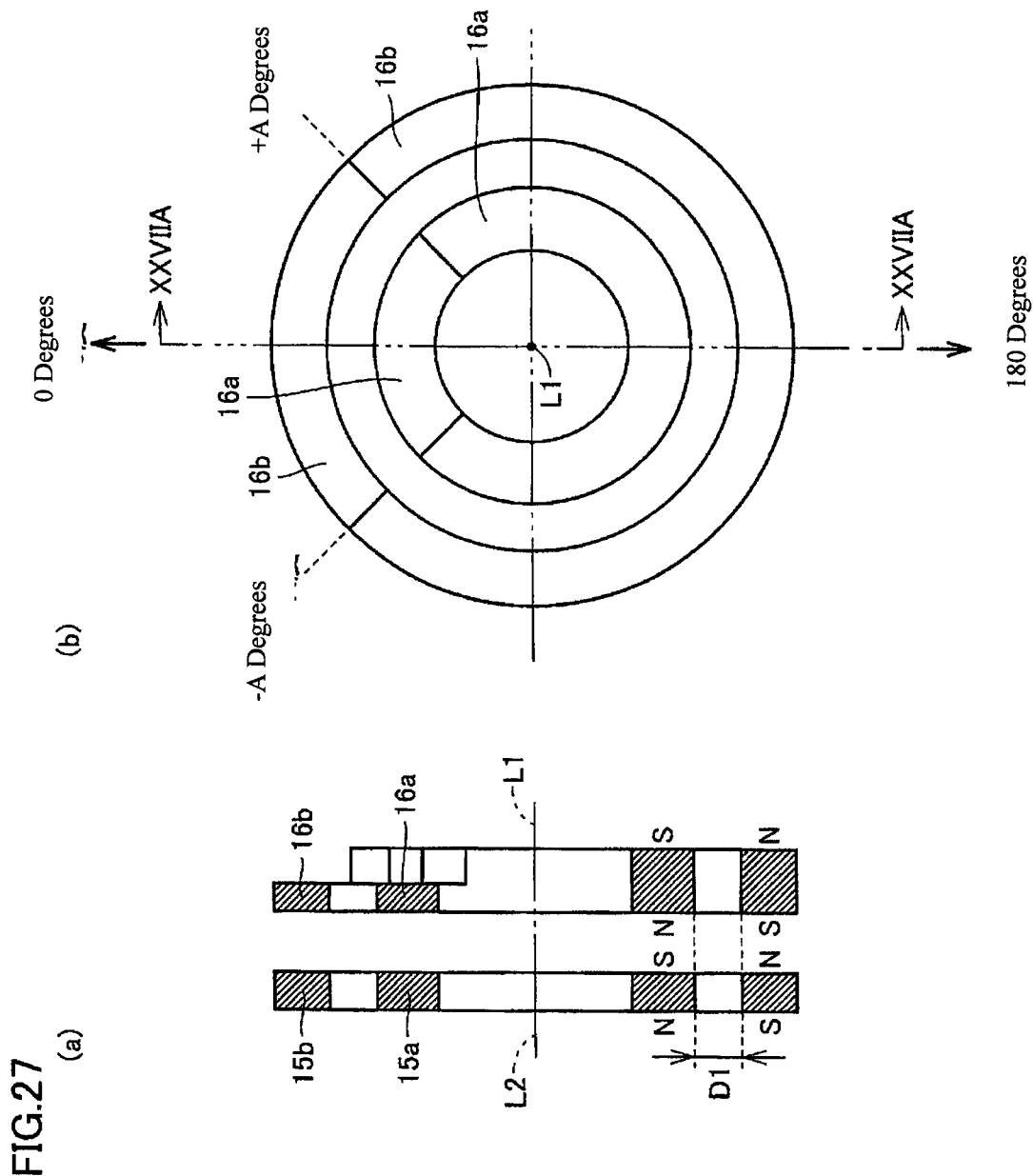
FIG. 27 is a drawing illustrating the configuration of the permanent magnet of the centrifugal blood pump device according to the third embodiment of this invention.

FIGS. 27 (a) and (b) are diagrams illustrating the configuration of permanent magnets 15a, 15b, 16a, 16b, and FIG. 27 (a) is a XXIIA-XXIIA line cross sectional view of FIG. 27 (b). In FIGS. 27 (a) and (b), a state is illustrated, where the center line L1 of the side wall of the cylinder of the blood chamber 7 and the center line L2 of the impeller 10. The permanent magnets 15a, 15b, respectively, are formed annularly and the outer diameter of the permanent magnet 15a is smaller than the inner diameter of the permanent magnet 15b. The permanent magnets 15a, 15b are formed coaxially, and the center point of the permanent magnets 15a, 15b are disposed on the rotation center line L2 of the impeller 10. The N-poles of the permanent magnets 15a, 15b are disposed to face opposing directions.

Meanwhile, the permanent magnets 16a, 16b, respectively, are formed in an arc shape. The outer diameter and inner diameter of the permanent magnet 16a are the same as the outer diameter and inner diameter of the permanent magnet 15a. The outer diameter and inner diameter of the permanent magnet 16b are the same as the outer diameter and inner diameter of the permanent magnet 15b. The permanent magnets 16a, 16b are provided coaxially, and the center point of the permanent magnets 16a, 16b are disposed on the center line L1 of the side wall of a cylinder of the blood chamber 7. The N-poles of the permanent magnets 16a, 16b face different directions. The S-poles of the permanent magnets 15a, 15b and the N-poles of the permanent magnets 16a, 16b mutually oppose each other.

Furthermore, as illustrated in FIG. 26, in order to make the attractive force of the permanent magnets 15a, 15b and the permanent magnets 16a, 16b in the opening 7a side (the range 0 degrees±A degrees) less than the attractive force of the permanent magnets 15a, 15b and the permanent magnets 16a, 16b, the thickness of the permanent magnets is thinned in the opening 7a side (the range 0 degrees±A degrees). Herein, A degrees is an angle predetermined greater than 0 degrees and less than 180 degrees. Preferably, A degrees is 60 degrees.

In other words in the range of 0 degrees±A degrees as viewed from the center point of the permanent magnets 16a, 16b, a concave portion with a prescribed depth is formed on the back surface of the permanent magnets 16a, 16b (the opposite side surface of the front surface opposing the permanent magnets 15a and 15b). As a result, the attractive force of the permanent magnets 15a, 15b the permanent magnets 16a, 16b in the opening 7a side is smaller than the attractive force of the permanent magnets 15a, 15b the permanent magnets 16a, 16b on the opposite side of the opening 7a, the impeller 10 can be parallel to the barrier wall 6 during rotation, and the impeller 10 can be prevented from contacting the inner wall of the blood chamber 7.

Note that, in the third embodiment, the prescribed portions of the permanent magnets 16a, 16b are thinned in order to suppress the incline (an angle of θ) of the rotational axis of the impeller 10, however, it is not limited to this: a notch may be made in the outer periphery of prescribed portions of the permanent magnets 16a, 16b, the width of the prescribed portions may be narrowed, the prescribed portions may be dropped, and the prescribed portions may be chamfered.

[Fourth Embodiment]

FIG. 28 is a cross sectional view illustrating a centrifugal pump device according to a fourth embodiment of the present invention, and is a diagram comparable to FIG. 4. Referring to FIG. 28, in this centrifugal pump device, a plurality of permanent magnets 17 are disposed to open a gap along a circle on the same angular interval so that the magnetic poles that are contacting are different. In other words, the permanent magnet 17 facing the N-pole of the motor chamber 8 side and the permanent magnet 17 facing the S-pole of the motor chamber 8 side are alternately disposed to open a gap along the circle in the same angular interval.

FIG. 29 (a) is a diagram illustrating the magnetic field between the permanent magnets 17, 17 in the fourth embodiment and FIG. 29 (b) is a diagram illustrating the magnetic field between the permanent magnets 17, 17 in the first embodiment. As can be seen from FIGS. 29 (a) and (b), if the weight of the permanent magnet 17 in the fourth embodiment and the weight of the permanent magnet 17 in the first embodiment are the same, the magnetic flux density between the permanent magnets 17, 17 in the fourth embodiment is larger, and the magnetic field in the periphery of the permanent magnet 17 in the fourth embodiment is stronger. Therefore, in the fourth embodiment, the magnetic coupling force between the permanent magnet 17 of the impeller 10 and the magnetic body 18 and the coils 20 in the motor chamber 8 can be strengthened. Further, the rotary torque of the impeller 10 can be increased while maintaining a small device size.

Figure 30:
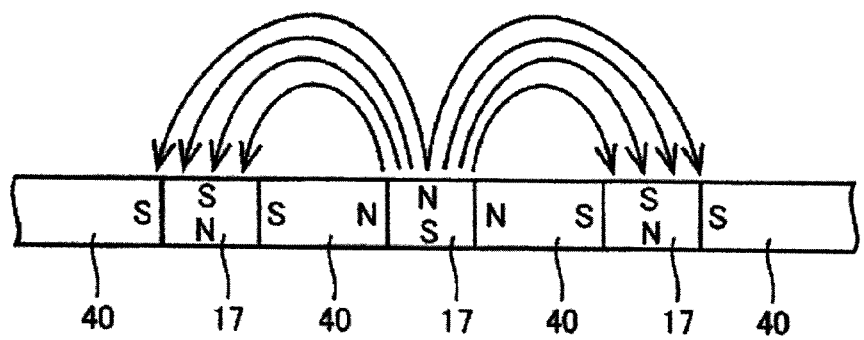
FIG. 30 is a drawing illustrating an alternative example of the fourth embodiment.

FIG. 30 is a diagram illustrating an alternative example of the fourth embodiment. In FIG. 30, in the alternative example, a plurality of permanent magnets 17 and a plurality of permanent magnets 40 are embedded in the shroud 12. The number of permanent magnets 40 is the same as the number of permanent magnets 17. The permanent magnets 40 are magnetized in the circumferential direction (the rotation direction of the impeller 10). The plurality of permanent magnets 17 and the plurality of permanent magnets 40 are disposed in a Halbach array configuration at equal angular intervals along the same circle one by one, alternately.

In other words, the permanent magnet 17 facing the N-pole of the barrier wall 6 side and the permanent magnet 17 facing the S-pole of the barrier wall 6 side are alternately disposed to provide a gap along the circle on the same angular interval. The N-poles of the permanent magnets 40 are disposed facing the permanent magnet 17 that faces the N-pole on the barrier wall 6 side, and the S-poles of the permanent magnets 40 are disposed facing the permanent magnet 17 that faces the S-pole on the barrier wall 6 side. The shape between the plurality of permanent magnets 17 is the same, and the shape between the plurality of permanent magnets 40 is the same. The shape of the permanent magnets 17 and the shape of the permanent magnets 40 may be the same or may be different.

In this alternative example, the magnetic flux that causes torque can be strengthened while the attractive force between the permanent magnet 17 and the magnetic body 18 is suppressed, therefore, the permanent magnets can be maximally miniaturized. That is, the impeller 10 can be its lightest weight, and the energy efficiency can be improved even when the motor gap is wide.

Figure 31:
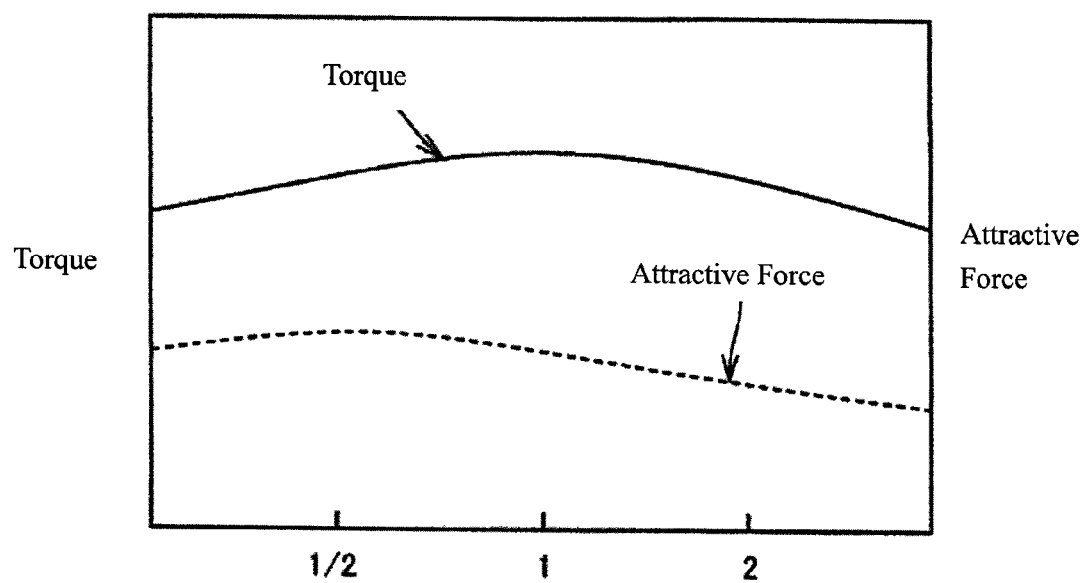
FIG. 31 is a drawing illustrating the optimal range of the area ratio of the permanent magnet 40 in relation to the permanent magnet 17 illustrated in FIG. 30.

Furthermore, the attractive force between the permanent magnet 17 and the magnetic body 18 and the magnetic flux that causes torque can be adjusted by comparing the area of the surface opposing the barrier wall 6 of the permanent magnet 17 and the area of the surface opposing the barrier wall 6 of the permanent magnet 40. FIG. 31 illustrates a relationship between the attractive force and the generated torque for when the total weight of the permanent magnet 17 and the permanent magnet 40 are the same, and when the area ratio of the permanent magnet 40 to the permanent magnet 17 is changed. As illustrated in FIG. 31, when the area ratio of the permanent magnet 40 to the permanent magnet 17 is set in a range of ½ to 2, the rotary torque of the impeller 10 can be increased while the attractive force between the permanent magnet 17 and the magnetic body 18 can be suppressed smaller. Therefore, the optimum range for the area ratio of the permanent magnet 40 to the permanent magnet 17 is between ½ and 2.

Note that, generally, when using a Halbach array for the purpose of reducing torque pulsation in the motor, the area of the permanent magnet 17 to the permanent magnet 40 is set from 5:1 to 3:1. In the present invention, in order to strengthen the magnetic field when the motor gap is wide, the area ratio of the permanent magnet 17 to the permanent magnet 40 can be optimized when set in a range from 2:1 to 1:2 according to the motor size and the motor gap.

[Fifth ]Embodiment

FIG. 32 (a) is a bottom view of a rotor 61 of an axial gap type motor according to a fifth embodiment of the present invention as viewed from a barrier wall 60 side, and FIG. 32 (b) is a front view that illustrates the main parts of the axial gap type motor.

In FIGS. 32 (a) and (b), this axial gap type motor has a similar composition as the centrifugal pump device 1 in the first to the fourth embodiments, and is provided with first and a second chambers (not illustrated) partition by a circular barrier wall 60. In the first chamber, an annular rotor provided rotatably along the barrier wall 60 is provided, and in the second chamber, a stator 70 that rotationally drives a rotor 61 through the barrier wall 60 is provided.

The rotor 61 includes an annular support material 62 formed with non-magnetic material and a plurality of permanent magnets 63 (for example 8) fixed to the support material 62. The plurality of permanent magnets 63 are arrayed with the gap opened together in the rotation direction of the rotor 61. The permanent magnets 63 are magnetized in the extension direction of the rotary center axis of the rotor 61. The magnetic poles of the two adjacent permanent magnets 63 are different from each other. The stator 70 includes a plurality (for example, 6) of magnetic bodies 71 disposed opposing the plurality of permanent magnets 63 and a plurality of coils 72 to generate a rotation magnetic field and wound on the plurality of magnetic bodies 71, respectively. The plurality of magnetic bodies 71 is fixed on an annular yoke 73. By applying voltage to a plurality of coils 72 in a 120 degree excitation method, the rotor 61 can be rotated.

Figure 33:
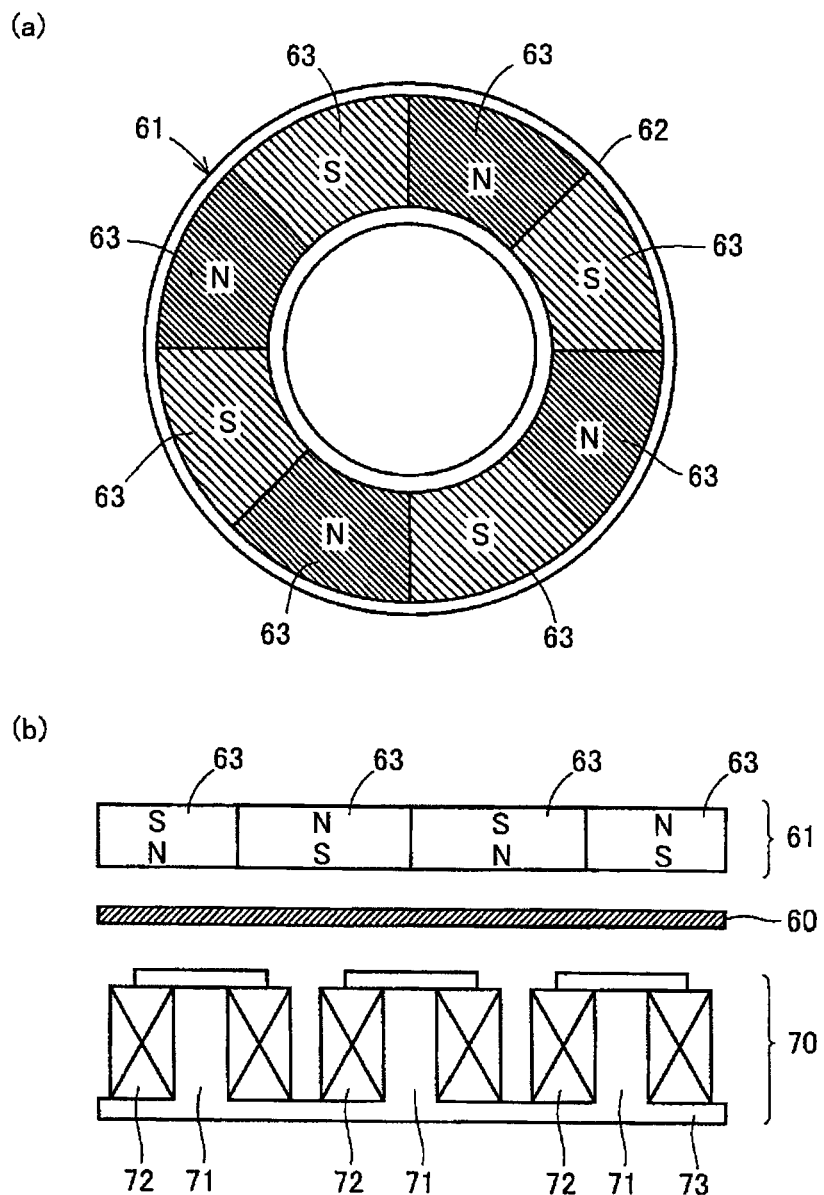
FIG. 33 is a drawing illustrating a comparative example of the fifth embodiment.

Next, an effect of the fifth embodiment is described. FIGS. 33 (a) and (b) are diagrams that illustrate a comparative example of the fifth embodiment and are diagram contrasted with FIGS. 32 (a) and (b). In FIGS. 33 (a) and (b), the point where this comparative example is different from the fifth embodiment is the point that there is no gap between the plurality of permanent magnets 63.

As illustrated in FIGS. 29 (a) and (b), if the weight of the permanent magnet 63 in the fifth embodiment and the weight of the permanent magnet 63 in the comparative example are the same, the magnetic flux density between the permanent magnets 63, 63 in the fifth embodiment is larger, and the magnetic field in the periphery of the permanent magnet 63 in the fifth embodiment is stronger. Therefore, in the fifth embodiment, the magnetic coupling force between the permanent magnet 63 of the rotor 61 and the magnetic body 71 and the coil 72 in the stator 70 can be strengthened. Further, the rotary torque of the rotor 61 can be enlarged while maintaining a small device size.

FIGS. 34 (a) and (b) are diagrams illustrating an alternative example of the fifth embodiment. In FIGS. 34 (a) and (b), in the alternative example, a plurality of permanent magnets 63 and a plurality of magnets 67 are embedded in the rotor 61. The number of permanent magnets 67 is the same as the number of permanent magnets 63. The permanent magnets 67 are magnetized in the circumferential direction (the rotation direction of the rotor 61). The plurality of magnets 63 and the plurality of magnets 67 are disposed in a Halbach array configuration in equal angular intervals along the same circle one by one, alternately. In other words, the permanent magnet 63 facing the N-pole of the barrier wall 60 side and the permanent magnet 63 facing the S-pole of the barrier wall 60 side are alternately disposed to provide a gap along the circle on the same angular interval. The N-poles of the permanent magnets 67 are disposed facing the permanent magnet 63 that faces the N-pole on the barrier wall 60 side, and the S-poles of the permanent magnets 67 are disposed facing the permanent magnet 63 that faces the S-pole on the barrier wall 60 side. The shape between the plurality of permanent magnets 63 is the same, and the shape between the plurality of permanent magnets 67 is the same. The shape of the permanent magnets 63 and the shape of the permanent magnets 67 may be the same or may be different. In this alternative example, the magnetic flux that is the cause of the torque can be strengthened while the attractive force between the permanent magnet 63 and the magnetic body 71 is suppressed, therefore, the permanent magnets can be maximally miniaturized (see FIG. 30). That is, the rotor 61 can be its lightest weight, and the energy efficiency can be improved even when the motor gap is wide.

Furthermore, the attractive force between the permanent magnet 63 and the magnetic body 71 and the magnetic flux that is the cause of the torque can be adjusted by comparing the area of the surface opposing the barrier wall 60 of the permanent magnet 63 and the area of the surface opposing the barrier wall 60 of the permanent magnet 67. As illustrated in FIG. 31, when the area ratio of the permanent magnet 67 to the permanent magnet 63 is set in a range of ½ to 2, the rotary torque of the rotor 61 can be increased while the attractive force between the permanent magnet 71 and the magnetic body 63 can be suppressed smaller. Therefore, the optimum range for the area ratio of the permanent magnet 67 to the permanent magnet 63 is between ½ and 2.

Note that, in a general motor, as illustrated in FIG. 33, the magnetic poles are often configured with only the permanent magnets 63. However, in the fifth embodiment, in the canned motor configuration with the barrier wall 60 is provided between the stator 70 and the rotor 61, regardless of whether it is a radial gap type or an axial gap type, there is a challenge that increasing torque and increasing efficiency is difficult because the gap between the stator 70 and the rotor 61 is large. In particular, when it is a small monitor, the freedom of design is lower due to constraints in size and the like, it is susceptible to local magnetic saturation, and increasing efficiency is difficult. However, by adopting the Halbach array as in this alternative example, even when the gap between the stator 70 and the rotor 61 is large, the field magnetic flux of the permanent magnet 63 can pass to the stator 70 efficiently. However, the motor torque can be increased without increasing the mass of the rotor 61, furthermore, without increasing the rigidity value in the axial direction from the wide motor gap. Further, the rotor 61 can be rotated at high speeds and the rotor 61 can startup rotation smoothly.

The embodiments disclosed herein are merely examples of all of the points and should not be thought of as restrictive. The scope of the present invention is not described above but is illustrated by the scope of the claims, and it is intended that scope of the claims or an equivalent meaning include all of the changes within the scope.

DESCRIPTION OF THE REFERENCE NUMERALS 1 pump portion, 2 housing, 3 main body, 4 blood inflow port, 5 blood outflow port, 6 barrier wall, 7 blood chamber, 8 motor chamber, 10 impeller, 10a through-hole, 11, 12 shroud, 13 vane, 14 blood passage, 15 to 17, 40, 63, 67 permanent magnet, 18, 35, 37 to 39, 71 magnetic body, 19, 36, 73 yoke, 20, 72 coil, 21, 22 hydrodynamic groove, 25 controller, 26 motor control circuit, 27, 30, 31 power amplifier, 32 changeover switch, 61 rotor, 70 stator

What is claimed is:

1. A centrifugal pump device, comprising:
a housing including a first and a second chamber divided by a barrier wall;
an impeller rotatably provided along the barrier wall in the first chamber that sends a liquid to an outflow port by centrifugal force during rotation of the impeller; and
a drive portion provided in the second chamber that rotatably drives the impeller with the barrier wall therebetween; and comprising
a first magnetic body provided on a first face of the impeller,
a second magnetic body provided on an inner wall of the first chamber opposing the first face of the impeller that attracts the first magnetic body, wherein the second magnetic body has a greater attractive force at a first portion of the housing proximate to the outflow port than at a second portion of the housing distal to the outflow port, and
a plurality of first permanent magnets provided on a second face of the impeller arranged along a circle such that adjacent magnetic poles are mutually different; wherein the drive portion includes a plurality of third magnetic bodies provided opposing the plurality of first permanent magnets, and
a plurality of coils provided corresponding to each of the plurality of third magnetic bodies wound around each corresponding third magnetic body to generate a rotating magnetic field;
a first attractive force between the first and the second magnetic bodies and a second attractive force between the plurality of first permanent magnets and the plurality of third magnetic bodies balance in a substantial center of a range of movement of the impeller in the first chamber during rotation of the impeller; and
a first hydrodynamic groove is formed on the first face of the impeller or on the inner wall of the first chamber facing thereto, and a second hydrodynamic groove is formed on the second face of the impeller or on the barrier wall facing thereto.

2. A centrifugal pump device according to claim 1, wherein the drive portion further includes a fourth magnetic body provided on a tip end surface opposing a first permanent magnet of the plurality of third magnetic bodies, and an area of a surface opposing a first permanent magnet of the fourth magnetic body is larger than an area of a tip end surface of the first permanent magnet of the plurality of third magnetic bodies.

3. The centrifugal pump device according to claim 2, wherein opposing surfaces of adjacent magnets of the fourth magnetic body are substantially parallel to each other.

4. The centrifugal pump device according to claim 1, wherein each third magnetic body includes a plurality of steel plates stacked in a length direction of a rotational axis of the impeller.

5. The centrifugal pump device according to claim 1, wherein each third magnetic body includes a plurality of steel plates stacked in a rotational direction of the impeller.

6. The centrifugal pump device according to claim 1, wherein each third magnetic body includes a plurality of steel plates stacked in a radial direction of the impeller.

7. The centrifugal pump device according to claim 1, wherein each third magnetic body is formed of a powder of pure iron, soft iron, or ferrosilicon.

8. The centrifugal pump device according to claim 1, wherein each of the first and second magnetic bodies is a permanent magnet.

9. A centrifugal pump device according to claim 1, further comprising a plurality of second permanent magnets provided on the second face of the impeller inserted respectively into a plurality of gaps in the plurality of first permanent magnets; wherein each second permanent magnet is magnetized in a rotational direction of the impeller, a first magnetic pole of each second permanent magnet faces one of the plurality of first permanent magnets such that the first magnetic pole faces one of the plurality of the first permanent magnets having its first magnetic pole facing the barrier wall, and a second magnetic pole of each second permanent magnet faces one of the plurality of first permanent magnets such that the second magnetic pole faces another of the plurality of the first permanent magnets having its second magnetic pole facing the barrier wall.

10. The centrifugal pump device according to claim 1, wherein a sum of an absolute value of a negative support rigidity value in an axial direction of the impeller provided by the first and second attractive forces and an absolute value of a positive rigidity value in a radial direction of the impeller is smaller than an absolute value of a positive rigidity value obtained by the first and second hydrodynamic grooves.

11. The centrifugal pump device according to claim 1, wherein a first hydrodynamic force generated by the first hydrodynamic groove is different than a second hydrodynamic force generated by the second hydrodynamic groove.

12. The centrifugal pump device according to claim 1, wherein at least one of the first and second hydrodynamic grooves is an inward spiral groove.

13. The centrifugal pump device according to claim 1, wherein a diamond-like carbon film is formed on at least one surface of the impeller or an inner wall of the first chamber to reduce frictional force.

14. The centrifugal pump device according to claim 1, wherein the liquid is blood, and the centrifugal pump device is used to circulate the blood.

15. The centrifugal pump device according to claim 1, wherein the second magnetic body having a greater attractive force at the first portion of the housing proximate to the outflow port than at the second portion of the housing distal to the outflow port comprises:

the second magnetic body comprising magnets located radially around a rotational axis of the impeller, wherein the first chamber has a circular inner wall and the outflow port tangentially intersects the circular inner wall, and wherein in an arc about the radius between the rotational axis of the impeller and the intersection of the outflow port with the circular inner wall, the magnets of the second magnetic body are smaller than the magnets of the second magnetic body outside the arc.

16. The centrifugal pump device according to claim 15, wherein the arc is centered on the radius between the rotational axis of the impeller and the intersection of the outflow port with the circular inner wall.

17. The centrifugal pump device according to claim 16, wherein the angular width of the arc is 120 degrees.

* * * * *